US005763404A

United States Patent [19]
Folkers et al.

[11] Patent Number: 5,763,404
[45] Date of Patent: Jun. 9, 1998

[54] METHODS FOR USING LHRH ANTAGONISTS WITH LOW HISTAMINE RELEASE

[76] Inventors: Karl A. Folkers, 6406 Mesa Dr., Austin, Tex. 78731; Cyril Y. Bowers, 484 Audubon St., New Orleans, La. 70118; Anders Ljungqvist, 3202 Whiteway, Austin, Tex. 78757; Pui-Fun Louisa Tang, Block R. Unit 505, Kornhill, Quarry Bay, Hong Kong, Hong Kong; Minoru Kubota, 5-12-4 Chiyoda, Yotsukaido-shi, Chiba 284, Japan; Dong-Mei Feng, 1141 Snyder Rd. #I-12, Lansdale, Pa. 19446

[21] Appl. No.: 466,333

[22] Filed: Jun. 6, 1995

Related U.S. Application Data

[60] Division of Ser. No. 371,552, Jun. 26, 1989, Pat. No. 5,470,947, which is a continuation-in-part of Ser. No. 88,431, PCT/US88/02922 filed on Aug. 24, 1988, Pat. No. 4,935,491.

[51] Int. Cl.$^6$ .......................... A61K 38/24; A61K 38/04; C07K 7/23
[52] U.S. Cl. ......................... 514/15; 530/313; 530/328
[58] Field of Search ............................. 514/15; 530/328, 530/313

[56] References Cited

U.S. PATENT DOCUMENTS

| | | | |
|---|---|---|---|
| 4,431,635 | 2/1984 | Coy et al. | 424/177 |
| 4,444,759 | 4/1984 | Rivier et al. | 424/177 |
| 4,504,414 | 3/1985 | Folkers et al. | 260/122.5 |
| 4,530,920 | 7/1985 | Nestor et al. | 514/15 |
| 4,647,653 | 3/1987 | Coy | 530/313 |
| 4,652,550 | 3/1987 | Rivier et al. | 530/313 |
| 4,801,577 | 1/1989 | Nestor, Jr. et al. | 514/15 |
| 4,845,077 | 7/1989 | Hodgen | 514/15 |
| 4,851,385 | 7/1989 | Roeske | 530/313 |
| 5,140,009 | 8/1992 | Haviv et al. | 514/16 |
| 5,180,711 | 1/1993 | Hodgen | 514/15 |
| 5,300,492 | 4/1994 | Haviv et al. | 514/15 |
| 5,413,990 | 5/1995 | Haviv et al. | 514/15 |

FOREIGN PATENT DOCUMENTS

| | | |
|---|---|---|
| A10 081 877 | 6/1983 | European Pat. Off. |
| A30 097 031 | 12/1983 | European Pat. Off. |
| A10 143 573 | 6/1985 | European Pat. Off. |
| A20 162 575 | 6/1985 | European Pat. Off. |
| A20 162 575 | 11/1985 | European Pat. Off. |
| A30 175 506 | 11/1985 | European Pat. Off. |
| A30 175 506 | 3/1986 | European Pat. Off. |
| A20 197 798 | 10/1986 | European Pat. Off. |
| A20 199 302 | 10/1986 | European Pat. Off. |
| A20 225 746 | 6/1987 | European Pat. Off. |
| A20 277 829 | 8/1988 | European Pat. Off. |
| 0328090 | 8/1989 | European Pat. Off. ............. 530/313 |

OTHER PUBLICATIONS

"Recovery of Pituitary–Gonadal Function in Male and Female Rats After Prolonged Administration of a Potent Antagonist of Luteinizing Hormone–Releasing Hormone (SB–75)," Lazaro Bokser et al., *Neuroendocrinology*, Aug. 1991, pp. 136–145.

"Blockade of Central and Peripheral Luteinizing Hormone–Releasing Hormone (LHRH) Receptors in Neonatal Rats With A Potent LHRH–Antagonist Inhibits the Morphofunctional Development of the Thymus and Maturation of the Cell–Mediated and Humoral Immune Responses," M. C. Morale et al., *Endocrinology*, vol. 128, No. 2, Feb. 1991, pp. 1073–1085.

"Effects of LHRH Antagonist Administration to Immature Male Rats on Sexual Development," H. M. Van Den Dungen et al., *Physiology & Behavior*, vol. 46, 1989, pp. 779–785.

"The Effects of LH–RH Inhibitory Analogues in the Non–Human Primate. Basic Studies in Contraception and Their Direct Applications for Future Clinical Uses in Both Sexes," Ricardo H. Asch, M.D., *LHRH and Its Analogues*, 1984, pp. 188–202.

(List continued on next page.)

*Primary Examiner*—Cecilia J. Tsang
*Assistant Examiner*—S. G. Marshall

[57] ABSTRACT

Antide is the decapeptide, N-Ac-D-2-Nal,D-pClPhe, D-3-Pal, Ser,NicLys, D-NicLys, Leu, ILys, Pro, D-Ala,NH$_2$ which is an antagonist of luteinizing hormone releasing hormone (LHRH). This decapeptide, like others of the present invention, has high antiovulatory activity (AOA) and releases negligible histamine. Antide is scheduled for scale-up, safety testing and evaluation in the experimental primate and in clinical medicine. Numerous other peptides having structures related to Antide were prepared and tested. These peptides had variations primarily in positions 5, 6, 7, and 8. Of these, N-Ac-D-2-Nal, D-pClPhe,D-3-Pal,Ser, PicLys,cis-DPzACAla,Leu,ILys,Pro,D-Ala-NH$_2$ was one of the most potent and had higher antiovulatory activity than Antide, i.e. 73%/0.25 ug and 100%/0.5 ug vs. 36%/0.5 ug and 100%/1.0 ug. Antide showed significant, (p<0.001) duration of action, when injected at a dose of 10 ug, 44 hours before 50 ng of the agonist, [D-3-Qal$^6$]-LHRH. Antide showed oral AOA at 600 ug (73%) and at 1200 ug (100%) with negligible difference being found between water and corn oil oral formulations.

In the antagonists prepared according to the present invention, arginine and its derivatives were not utilized. Lysine was converted into derivatives with acyl groups or with alkyl groups on the E-amino group. The amino acid ornithine was acylated or alkylated on the d-amino group. Both the L- and D- forms of lysine and the L-form of ornithine were used in synthesizing these acyl and alkyl derivatives. Structurally related intermediates were also synthesized. All together, many new peptides were synthesized by the basic and minimal concepts of ten variables for anti-ovulation activity and ten variables for histamine release, which may be independent or partially overlapping. On such a basis, the number of such peptides that can be designed becomes overwhelming, and every reasonable priority must be considered to reduce the number of peptides to be synthesized in the hope that a discovery will be realized.

43 Claims, No Drawings

OTHER PUBLICATIONS

"Effects of a Luteinizing Hormone–Releasing Hormone Antagonist in Late–Juvenile Female Rats: Blockade of Follicle Growth and Delay of First Ovulation Following Suppression of Gonadotropin Concentrations," H. M. A. Meijs–Roelofs et al., *Biology of Reproduction*, vol. 43, No. 4, Oct. 1990, pp. 607–613.

Channabasaviah, et al., *New Potent Agonist and Antagonist Analogs of Luteinizing Hormone Release Hormore*, pp. 803–806.

Hautklinik, et al., *Archiv der Pharmazie*, vol. 7, pp. 330–338 (1958).

Chemical Abstract, 10B–*Aliphatic Compounds*, pp. 11237–11238, (U.S. Patent No. 2,872,484)(1959).

Benoiton, *Canadian Journal of Chemistry*, vol. 42, pp. 2043–2047 (1964).

Bernardi, et al. *J. Pharm. Pharmac.*, vol. 19, pp. 95–101 (1967).

Tjoeng, et al., *Chem. Ber.*, vol. 108, pp. 862–874 ( 1975).

Prasad, et al., *Journal of Medicinal Chemistry*, vol. 19, pp. 492–495 (1976).

Humphries, et al., *Journal of Medicinal Chemistry*, vol. 21,120–123 (1978).

Channabasaviah, et al., *Biochem and Biohpys Research Comm.*, vol. 86, No. 4, pp. 1266–1275 (1979).

Nikolis, et al., *Peptides*, vol 5, pp. 1001–1006 (1984).

Fife and Przystas, *J. Am. Chem. Soc.*, vol. 4, pp. 1041–1047 (1985).

Karten and Rivier, *J. Endocrine Rev.*, vol. 7, No. 1, pp. 44–66 (1986).

Rivier et al., *J. Med. Chem.*, vol. 29, pp. 1846–1851 (1986).

Karten, Marvin J., *J. Endocrine Rev.*, vol. 7, No. 1, pp. 44–66 (1986).

Roeshe, et al. Proceedings of 9th American Peptide Sym Pierce Chem. Co., Rockford, IL, pp. 561–564 (1986).

Folkers, et al., Z. Naterfarsch, *B. Chem. Sci.* 42(1), pp. 101–106 (1987).

Hocart, S.J., et al. *J. Med. Chem.* 30(10), pp. 1910–1914, Oct. (1987).

Ljungvist, et al., *Biochem Biophys. Res. Commun.*, vol. 148, No. 2, pp. 849–856, (1987).

Hocart, S. J., et al. *J. Med. Chem.* 30, pp. 739–743 (1987).

Karten et al., *Contraceptive and Therapeutic Applications*, Part 2 eds., Vickery et al., pp. 179–190 (1987).

Bajusz et al., *Proc. Natl. Acad. Sci. USA*, vol. 85, pp. 1637–1641 (1988).

Rivier, et al., *Coll. Soc. Etides Fertil.*, vol. 26, pp. 25–31 (1988).

Dutta, Anand S., *Drugs of the Future*, vol. 13, No. 8, pp. 761–767 (1988).

River, et al., *J. Med. Chem.*, vol. 29, pp. 1846–1851 (1986).

Phillips, et al., *Life Sciences*, vol 43, pp. 883–888 (1988).

PCT International Search Report, mailed Jan. 27, 1989.

Nestor, J.J., Tahilramani, R., Ho, T. L., McRae, G. I. & Vickery, B.H. (1988) *J. Med. Chem.* vol. 31, No. 1, pp. 65–72.

Rivier, J. Kupryszewski, G., Varga, J., Porter, J., Rivier, C., Perrin, M., Hagler, A., Struthers, S., Corrigan, A. & Vale, W. (1988) *J. Med. Chem.* vol. 31, No. 3, pp. 677–682.

Folkers, K., Bowers, C.Y., Shieh, H.–M., Liu, Y.–Z., Xiao, S.–B., Tang, P.–F.L. & Chu, J.–Y. (1984) *Biochem. Biophys, Res. Commun.*, vol. 123, No. 3, pp. 1221–1226.

Miyamoto, K., Hasegawa, Y., Nomura, M., Igarashi, M., Kanagawa, K. & Matsuo, H. (1984) *Proc. Natl. Acad. Sci, USA*, vol. 81, No. 12, 3874–3878.

Sherwood, N., Eiden, L., Brownstein, M., Spiess, J., Rivier, J., & Vale, W. (1983) *Proc. Natl. Acad. Sci. USA*, vol. 80, No. 9, pp. 2794–2798.

Sherwood, N.M., Sower, S.A., Marshak, D.R., Fraser, B.A. & Brownstein, M.J. (1986) *J. Biol. Chem.* vol. 26, No. 11, pp. 4812–4819.

Roeske, R.W., Chaturvedi, N.C., Hrinyo–Pavlina, T., Kowalczuk, M., *LHRH and Its Analogs: Contraceptive and Therapeutic Applications Part 2*, eds. Vickeryk, B.H. & Nestor, J.J., Jr., (MTP Press Ltd., Lancaster, England) pp. 17–24.

Karten, et al. (1987), In Vitro histamine release with LHRH analogs;.

Bernardi, et al. (1967), *J. Pharm. Pharmac.*, 19:95–101;.

Hautklinik, et al., (1958), *Archiv der Pharmazie*, No. 7:330–338;.

Fife and Przystas, (1985), *J. Am. Chem. Soc.*, 4:1041–1047;.

Prasad, et al., (1976), *Journal of Medicinal Chemistry*, 19:492–495;.

Benoiton, (1964), *Canadian Journal of Chemistry*, 42:2043–2047;.

Chemical Abstract, (1959), 10B–Aliphatic Compunds, pp. 11237–11238 (U.S. patent No. 2,872,484);.

Tjoeng, et al., (1975), *Chem. Ber.*, 108:862–874;.

Humphries, et al. (1978), *Journal of Medicinal Chemistry*, 21:120–123;.

Karten, Marvin J., Endocrine Rev., vol. 7, No. 1, 1986, pp. 44–66.

Dutta, Anand S., Drugs of the Future, vol. 13, No. 8, 1988, pp. 761–767.

Phillips, et al., Life Sciences, vol. 43, 1988, pp. 883–888.

Rivier, et al., J. Med. Chem., 1986, 29, 1846–1851.

Rivier et al., (1986) New Effective Gonadotropin Releasing Hormone Antagonists with Minimal Potency for Histamine Release In Vitro, J. Med. Chem. 29:1846–1851.

Karten and Rivier, (1986) Gonadotropin–Releasing Hormone Analog Design. Structure–Function Studies Toward the Development of Agonists and Antagonists: Rationale and Perspective, Endocrine Reviews 7(1):44–66.

Ljungqvist et al., (1987) Design, Synthesis and Bioassays of Antagonists of LHRH Which Have High Antiovulatory activity and Release Negligible histamine, Biochem. and Biophys. Resh. Comm. 148(2):849–856.

Bajusz et al., (1988) Highly potent antagonists of luteinizing hormone–releasing hormone free of edematogenic effects, Proc. Natl. Acad. Sci USA 85:1637–1641.

Karten et al., (1987) LHRH and its analogs; contraceptive and therapeutic application Part 2, eds. Vickery et al., 179–190.

Hocart, S.J. ; et al. J. Med. Chem., 30(10) pp. 1910–1914, Oct. 1987.

Hocart, S.J. ; et al., J. Med. Chem., 30, pp. 739–743, 1987.

Roeshe; et al., *Peptides: Structure and Function*, Proceedings of 9th American Peptide Sym., Pierce Chem. Co., Rockford, IL. 561–564 1986.

Ljungqvist; et al. Biochem Biophys. Res. Commun, 148, pp. 849–856, 1987.

Folkers, et al., Z. Naterforsch, B.: Chem. Sci., 42(1), pp. 101–106, 1987.

Channabasavaich et al, Biochem. and Biophys. Research Comm., vol. 86, No. 4, (1979), pp. 1266–1273.

Rivier et al, Coll. Soc. Ekides Fertil., vol. 26, pp. 75–81 (1988).

Channabasvaiah et al., "New Potent Agonist and Antagonist Analogs of LHRH", pp. 803–806.

Nikolics et al, *Peptide* vol. 5, pp. 1001–1006,(1984).

Karten et al, Endocrine Reviews, vol. 7, No. 1, (1981).

Ljungqvist, et al, Biochemical and Biophysical Research Communication, pp. 849–856, 1987.

METHODS FOR USING LHRH ANTAGONISTS WITH LOW HISTAMINE RELEASE

This application is a divisional of application Ser. No. 07/371,552, filed Jun. 26, 1989 now U.S. Pat. No. 5,470,947; which is a continuation-in-part of U.S. patent application Ser. No. 07/088,431 filed Aug. 24, 1987 now U.S. Pat. No. 4,935,491, issued Jun. 19, 1990 which is a continuation of International Application No. PCT/US 88/02922 having the International Filing Date of Aug. 24, 1988.

Research related to the development of this invention was supported in part by the Contraceptive Branch of the National Institutes of Child Health and Human Development, contract no. NOI HD-6-2938 and to the Robert A. Welch Foundation.

BACKGROUND OF THE INVENTION

The present invention involves the design, synthesis and use of synthetic analogs of the luteinizing hormone releasing hormone (LHRH). An important achievement involved synthesis of analogs which functioned as antagonists of LHRH, were adequately potent to inhibit ovulation and allowed the release of only negligible amounts of histamine. Since there was no way of reliably forecasting the structure of an antagonist having high potency and very low histamine release, it was necessary to explore diverse approaches to discover a combination of structural features which would yield an antagonist of LHRH having high potency for ovulation inhibition and very low activity for histamine release.

Various peptides such as substance P, vasoactive intestinal peptide, gastrin, somatostatin, as well as others, are well known to cause the release of histamine from mast cells. These cells are in many tissues, such as skin, lung and mesentery, gingiva, etc. Most cells have granules containing histamine and other mediators of inflammation which can be released by peptides to cause capillary dilation and increased vascular permeability. When it was noted that an antagonist of LHRH, for example [Ac-D-2-Nal$^1$,D-4-F-Phe$^2$,D-Trp$^3$, D-Arg$^6$]-LHRH, caused edema of the face and extremities when it was administered to rats, it appeared likely that such antagonists, if administered to human subjects as a contraceptive agent, would cause serious edema of the face and elsewhere in the human body. Such side effects would likely prevent the administration of such antagonists to human subjects.

The histamine-containing leukocyte is a basophile which can also release histamine when stimulated by many of the same peptides mentioned above. Basophiles differ biochemically from mast cells and such differences may allow for both predictable and unpredictable histamine release in response to antagonists of LHRH. An antagonist of LHRH, to be used clinically to prevent ovulation, should not significantly release amounts of histamine from either mast cells or basophiles.

The discovery of the side effects such as the edematogenic and anaphylactoid actions of LHRH antagonists made desireable the discovery of new LHRH antagonists which prevented ovulation but did not release significant histamine. These undesireable side effects have been observed in rats, and it is likely that the Food and Drug Administration would not allow the testing of such antagonists in human subjects.

Karten et al. (4), have reviewed available knowledge on the structural characteristics for potent histamine release by antagonists of LHRH. Some of the most important findings are as follows. A most potent LHRH antagonist in triggering histamine release in vitro involved a combination of strongly basic D-amino acid side chains (Arg or Lys) at position 6 and in close proximity to Arg$^8$, and a cluster of hydrophobic aromatic amino acids at the N-terminus. Thus, there is no specific amino acid of the ten amino acids which is solely responsible for histamine release. On the contrary, structural features ranging from the N-terminus (the amino acids in the first few positions, 1–4, etc.), and basic amino acids toward the C-terminus (positions 6 and 8) somehow participate in histamine release. Even D-Ala in position 10 has some influence on histamine release, the rationale for which is unclear. By themselves, two basic side chains in close proximity, as in positions 6 and 8, are insufficient alone to impart high release of histamine. The cluster of hydrophobic amino acids at the N-terminus is insufficient alone for high histamine releasing activity. Even a hexapeptide fragment has revealed moderate histamine releasing potency. There seems to be no correlation between antiovulatory potency and histamine release of these antagonists, in vitro.

In perspective, much of the entire chain of such decapeptide antagonists may have influence on histamine release. The same perspective appears to be true, but to different degrees, for high antiovulatory activity. These LHRH antagonists are usually decapeptides which indicates that there are ten variables to adjust for a desired anti-ovulatory activity and ten variables to adjust for eliminating histamine releasing activity. There are even further variations for each of these twenty variables, the number of possible peptides to design, synthesize and assay becoming incalculable. Presumably, some of the ten variables may be independent for anti-ovulatory activity and histamine releasing activity while some variables may overlap for these two biological activities. This situation presents extraordinary difficulties to solve before an antagonist of high potency for anti-ovulation and very low potency for histamine release could be produced.

Diverse structural changes and combinations of the ten amino acids followed by assays of both anti-ovulation and histamine release activities should be performed in the hope that a potent antagonist essentially free of side effects would be discovered. The synthesis of new amino acids to introduce into the decapeptide chains should also be explored since the commonly available amino acids might not suffice.

SUMMARY OF THE INVENTION

In the antagonists prepared according to the present invention, arginine and its derivatives were not utilized. Lysine was converted into derivatives with acyl groups or with alkyl groups on the E-amino group. The amino acid ornithine was acylated or alkylated on the d-amino group. Both the L- and D- forms of lysine and the L-form of ornithine were used in synthesizing these acyl and alkyl derivatives. Structurally related intermediates were also synthesized. All together, many new peptides were synthesized by the basic and minimal concepts of ten variables for anti-ovulation activity and ten variables for histamine release, which may be independent or partially overlapping. On such a basis, the number of such peptides that can be designed becomes overwhelming, and every reasonable priority must be considered to reduce the number of peptides to be synthesized in the hope that a discovery will be realized.

Certain peptides were synthesized, tested and found to demonstrate advantageous peptides. Among these desireable peptides were the following two.

[N-Ac-D-2-Nal$^1$, D-pClPhe$^2$,D-3-Pal$^3$,NicLys5,D-NicLys$^6$,ILys$^8$,D-Ala$^{10}$]-LHRH was effective to prevent ovulation and released remarkably little histamine.

[N-Ac-D-2-Nal$^1$,D-pClPhe$^2$,D-3-Pal$^3$,PicLys$^5$,D-PicLys$^6$, ILys$^8$,D-Ala$^{10}$]-LHRH was twice as effective as the above peptide, and released no more histamine than do "super agonists" of LHRH, which are presently being marketed by several pharmaceutical companies.

These two new peptides, and yet additional related peptides described herein provide acceptable balances of high anti-ovulatory activity and low histamine release for full potential clinical utility.

The present invention involves the preparation and use of decapeptides having antiovulatory activity and with minimal histamine-releasing effects. These decapeptides includes those comprising:

Ser$^4$, PicLys$^5$ and D-PicLys$^6$;
N-Ac-D-2-Nal$^1$, D-pClPhe$^2$, Ser$^4$, D-PicLys$^5$ and Pro$^9$;
N-Ac-D-2-Nal$^1$, D-pClPhe$^2$, D-3-Pal$^3$, Ser$^4$, D-PicLys$^6$, Pro$^9$ and D-Ala$^{10}$;
N-Ac-D-2-Nal$^1$, D-pClPhe$^2$, D-3-Pal$^3$, Ser$^4$, NicLys$^5$, Pro$^9$ and D-Ala$^{10}$;
N-Ac-D-2-Nal$^1$, D-pClPhe$^2$, D-3-Pal$^3$, Ser$^4$, Leu$^7$, Pro$^9$ and D-Ala$^{10}$;
N-Ac-D-2-Nal$^1$, D-pClPhe$^2$, D-3-Pal$^3$, Ser$^4$, Leu$^7$, Pro$^9$ and D-Ser$^{10}$;
D-pClPhe$^2$, Pro$^9$ and D-Ala$^{10}$;
D-pClPhe$^2$, Pro$^9$ and Ser$^{10}$;
N-Ac-D-2-Nal$^1$, D-pClPhe$^2$, D-3-Pal$^3$, NicLys$^5$, D-NicLys$^6$, ILys$^8$ and D-Ala10;
N-Ac-D-2-Nal$^1$, D-pClPhe$^2$, D-3-Pal$^3$, NicLys$^5$, D-NicLys$^6$, ILys$^8$ and D-Ala$^{10}$;
N-Ac-D-2-Nal$^1$, D-pClPhe$^2$, D-3-Pal$^3$, PicLys$^5$, D-PicLys$^6$, ILys$^8$ and D-Ala$^{10}$;
N-Ac D-2-Nal$^1$, D-pClPhe$^2$, D-3-Pal$^3$, NicLys$^5$, D-NicLys$^6$, IOrn$^8$ and D-Ala$^{10}$;
N-Ac-D-2-Nal$^1$, D-pClPhe$^2$, D-3-Pal$^3$, PicLys$^5$, D-PicLys$^6$, IOrn$^8$ and D-Ala$^{10}$;
N-Ac-D-2-Nal$^1$, D-pClPhe$^2$, D-3-Pal$^3$, MNicLys$^5$, D-MNicLys$^6$, IOrn$^8$ and D-Ala$^{10}$;
N-Ac-D-2-Nal$^1$, D-pClPhe$^2$, D-3-Pal$^3$, PzcLys$^5$, D-PzcLys$^6$, IOrn$^8$ and D-Ala$^{10}$;
N-Ac-D-pClPhe$^1$, D-3-Pal$^3$, Tyr$^5$, D-NicLys$^6$ and ILys$^8$;
N-Ac-D-Cl$_2$Phe$^1$, D-3-Pal$^3$, Tyr$^5$, D-NicLys$^6$ and ILys$^8$;
acylated Lys$^5$, D-acylated Lys$^6$ and N-alkylated diamino acid$^8$;
NicLys$^5$, D-NicLys$^6$ and ILys$^8$;
PicLys$^5$, D-PicLys$^6$ and ILys$^8$;
NicLys$^5$, D-NicLys$^6$ and IOrn$^8$;
PicLys$^5$, D-PicLys$^6$ and IOrn$^8$;
MNicLys$^5$, D-MNicLys$^6$ and IOrn$^8$;
PzcLys$^5$, D-PzcLys$^6$ and IOrn$^8$;
Tyr$^5$, D-NicLys$^6$ and ILys$^8$;
Tyr$^5$, D-NicLys$^6$ and IOrn$^8$;
N-Ac-D-2-Nal$^1$, D-pClPhe$^2$, D-3-Pal$^3$, Ser$^4$, NicLys$^5$, D-NicLys$^6$, Leu$^7$, ILys$^8$, Pro$^9$ and D-Ala$^{10}$NH$_2$; and
N-Ac-D-2-Nal$^1$, D-pClPhe$^2$, D-3-Pal$^3$, Ser$^4$, PicLys$^5$, cis D-PzACAla$^6$, Leu$^7$, ILys$^8$, Pro$^9$ and D-Ala$^{10}$NH$_2$.

The present invention further involves use of the above decapeptides in a process for inhibiting ovulation in an animal. This process comprises administering to said animal a decapeptide preferably having the structure: N-Ac-D-2-Nal$^1$, D-pClPhe$^2$, D-3-Pal$^3$, Ser$^4$, NicLys$^5$, D-NicLys$^6$, Leu$^7$, ILys$^8$, Pro$^9$ and D-Ala$^{10}$NH$_2$. Likewise, the inventive process may be used to inhibit ovulation in an animal; to inhibit the onset of puberty in an animal; to inhibit the sexual impetus of an animal; to alter the gonadal function of an animal; to inhibit the growth of hormone-dependent tumors in an animal; and to lower LH and FSH levels in serum of post-menopausal women. These and other related uses will be apparent to those skilled in the art upon examination of this specification.

DESCRIPTIONS OF PREFERRED EMBODIMENTS

Abbreviations and formulas used herein include the following:

| | | |
|---|---|---|
| a | = | alpha |
| BOC | = | t-butoxycarbonyl |
| Br—Z | = | o-bromobenzyloxycarbonyl |
| nBuOAc | = | n-butylacetate |
| n-BuOH | = | n-butanol |
| c | = | cis |
| CDCl$_3$ | = | deuterochloroform |
| CHCl$_3$ | = | chloroform |
| CH$_2$Cl$_2$ | = | dichloromethane |
| CH$_3$CN | = | acetonitril |
| Cl—Z | = | o-chlorobenzyloxycarbonyl |
| d | = | delta |
| DCC | = | dicyclohexylcarbodiimide |
| DIEA | = | diisopropylethylamine |
| DMF | = | dimethylformamide |
| E | = | epsilon |
| Et | = | ethyl |
| EtOAc | = | ethyl acetate |
| EtOH | = | ethanol |
| Et$_2$O | = | diethyl ether |
| HF | = | hydrogen fluoride |
| HOAc | = | acetic acid |
| KH$_2$PO$_4$ | = | potassium dihydrogen phosphate |
| MeOH | = | methanol |
| MgSO$_4$ | = | magnesium sulfate |
| NH$_4$OAc | = | ammonium acetate |
| iPrOH | = | 2-propanol |
| py | = | pyridine |
| t | = | trans |
| TFA | = | trifluoroacetic acid |
| THF | = | tetrahydrofuran |
| TOS | = | p-toluensulfonyl |
| u | = | micro |
| Z | = | benzyloxycarbonyl |
| Abu | = | 2-aminobutyric acid |
| ACAla | = | aminocyclohexylalanine |
| Aile | = | alloisoleucine |
| AnGlu | = | 4-(4-methoxyphenylcarbamoyl)-2-aminobutyric acid |
| BzLys | = | N$^E$-benzoyllysine |
| Cit | = | citrulline |
| Cl$_2$Phe | = | 3,4-dichlorophenylalanine |
| CypLys | = | N$^E$-cyclopentyllysine |
| DMGLyS | = | N$^E$-N,N-dimethylglycyl)lysine |
| Dpo | = | N$^d$-(4,6-dimethyl-2-pyrimidyl)ornithine |
| Et$_2$hArg | = | N$^G$,N$^G$-diethylhomoarginine |
| FPhe | = | A-fluorophenylalarine |
| HOBLys | = | N$^E$-(4-hydroxybenzoyl)lysine |
| Ilys | = | N$^E$-isopropyllysine |
| INicLys | = | N$^E$-isonicotinoyllysine |
| IOrn | = | N$^d$-isopropylornithine |
| Me$_3$Arg | = | N$^G$,N$^G$,N$^{G1}$-trimethylarginine |
| Me$_2$Lys | = | N$^E$,N$^E$-dimethyllysine |
| MNicLys | = | N$^E$-(6-methylnicotinoyl)lysine |
| MPicLys | = | N$^E$-(6-methylpicolinoyl)lysine |
| NACAla | = | 3(4-nicotinoylaminocyclohexyl)alanine |
| 2-Nal | = | 3-(2-naphthyl)alanine |
| NicLys | = | N$^E$-nicotinoyllysine |
| NicOrn | = | N$^d$-nicotinoylornithine |
| Nle | = | norleucine, 2-aminohexanoic acid |
| NMeLeu | = | N-methylleucine |
| Nval | = | norvaline, 2-aminopentanoic acid |
| PACAla | = | 3(4-picolinoylaminocyclohexyl)alanine |
| 3-Pal | = | 3-(3-pyridyl)alanine |
| pClPhe | = | 3-(4-chloro)phenylalanine |
| PicLys | = | N$^E$-picolinoyllysine |
| Pip | = | piperidine-2-carboxylic acid |

| | | |
|---|---|---|
| PmcLys | = | N$^E$-(4-pyrimidinylcarbonyl)lysine |
| PmACAla | = | 3[4(4-pyrimidinylcarbonyl)aminocyclohexyl]alanine |
| PzACAla | = | 3(4-pyrazinylcarbonylaminocyclohexyl)alanine |
| 3-PzAla | = | 3-pyrazinylalanine |
| PzcLys | = | N$^E$-pyrazinylcarbonyllysine |
| Sar | = | N-methylglycine |
| TinGly | = | 3-thienylglycine |

Most natural amino acids were obtained from Peninsula Laboratories, San Carlos, Calif. The hydroxyl group of Ser was protected as the benzyl ether, the phenolic hydroxyl group of Tyr as the Br-Z derivative, and E-amino group of Lys as the Cl-Z derivative, the guanidino group of Arg and the imidazole group of His as the TOS derivatives. The a-amino function was protected as the BOC derivative. BOC-Orn(Z) was obtained from Sigma Chemical Co., St. Louis, Mo. BOC-D-2-Nal, BOC-D-3-Pal, BOC-D-Cl$_2$Phe, BOC-pClPhe and BOC-ILys(z) dicyclohexylamine salt were provided by the Southwest Foundation for Biomedical Research, San Antonio, Tex. The benzhydrylamine hydrochloride resin was obtained from Beckman Bioproducts, Palo Alto, Calif. The nitrogen content was about 0.65 mmoles/g. The CH$_2$Cl$_2$ was distilled before use.

The present invention involves the design, synthesis and use of LHRH antagonists with high antiovulatory potency and diminished activity to release histamine (1). These new antagonists feature, for example, D-N$^E$-nicotinoylisine (D-NicLys) in position 6 and N$^E$-isopropyllysine (ILys) in position 8. The solution of D-Arg$^6$, particularly in combination with Arg$^8$ and a cluster of hydrophobic aromatic amino acid residues at the N-terminal, have been implicated in the release of histamine (2–4).

Other reductions of anaphylactoid activity were obtained by increasing the distance between the positive charges in positions 6 and 8 by Arg$^5$ and by inclusion of a neutral residue in position 6 as in [N-Ac-D-2-Nal$^1$, D-pClPhe$^2$,D-3-Pal$^3$,Arg$^5$,D-4 (p-methoxybenzoyl)-2-aminobutyric acid$^6$, D-Ala$^{10}$]-LHRH (2-Nal represents 3-(2-naphthyl) alanine; PClPhe represents 3(4-chlorophenyl)alanine; 3-Pal represents 3(3-pyridyl)alanine) by Rivier et al. (5) and [N-Ac-D-2-Nal$^1$,D-aMepClPhe$^2$,D-Trp$^3$,Arg$^5$,D-Tyr$^6$,D-Ala$^{10}$]-LHRH (aMepClPhe represents 2 methyl-3(4-chlorophenyl) alanine) by Roeske et al. (6). Further modifications in position 6 are reductive alkylation of D-Lys$^6$ by Hocart et al. (7), incorporation of N,N-diethylhomoarginine by Nestor et al. (8). The cyclic analogs recently synthesized by Rivier et al. did not show any lowering in histamine release compared to the linear counterparts (10).

From the peptides of the present invention, two were initially selected as models for further design. The peptide [N-Ac-D-2-Nal$^1$, D-pClPhe$^2$, D-3-Pal$^3$, NicLys$^5$, D-NicLys$^6$, ILys$^8$, D-Ala$^{10}$]-LHRH (named Antide) had an impressive combination of potency and low histamine release; antiovulatory activity (AOA) was 100% at lug and 36% at 0.5 ug; ED$_{50}$ for histamine release, in vitro, was consistently above 300 ug/ml as compared to about 0.17 for the standard analog [N-Ac-D-2-Nal$^1$,D-pFPhe$^2$,D-Trp$^3$,D-Arg$^6$]-LHRH (pFPhe represents 3(4-fluorophenyl)alanine) (5). Another analog was identical to Antide except for PiCLys$^5$ and D-PiCLys$^6$ (PicLys represents N-picoloyllysine); 100% AOA at 0.5 ug and 40% at 0.25 ug; ED$_{50}$, 93±11.

Included herein are results from IMRH analogs with acylated aminocyclohexylalanine residues in position 6, from analogs in which Leu$^7$ has been substituted with other neutral residues, from a comparison of ILys$^8$ vs. IOrn$^8$, and from tests on oral activity and duration of antagonists activity when administered orally or parenterally (s.c.)

Melting points are uncorrected. NMR data are reported as d-values downfield from TMS.

Before acylation, the Z and Cl-Z groups of Lys and Orn were cleaved by hydrogenolysis in MeOH in the presence of 10% Pd/C.

BOC-D-BzLys was synthesized by acylation of BOC-D-Lys with benzoyl chloride as described for the L- isomer by Bernardi et al. (17).

BOC-DMG-Lvs was prepared by acylation of BOC-Lys with chloracetyl chloride using the same method and the reacting the crude product from 10 mmoles BOC-Lys in 10 ml THF with 10 ml 40% aq. dimethylamine. The reaction mixture was stirred 15 minutes in ice bath and then 2.5 hours at room temperature. After evaporation in vacuo the crude product was dissolved in 10 ml H$_2$O and applied on a Bio-Rad AG1-X8 column, acetate form, 1×25 cm. The column was first washed with 200 ml water and then the product was eluted with 6% HOAc and lyophilized several times to remove the HOAc. Yield 60–70%. Amorphous mass. R$_f$ (n-BuOH:py:HOAc:H$_2$O=30:10:3:12)=0.27. Purity>95%. NMR (CDCl$_3$):1.45,s,9H,t-butoxy group; 1.85– 1.48,m,6H,B,y,d,CH$_2$ groups; 2.6,s,6H,N(CH$_3$)$_2$; 3.25,m,2H, E-CH$_2$; 3.37,s,2H,N—CH$_2$—CO; 4.15,m,1 H,a-CH.

The other acylated Lys derivatives in the tables were prepared from BOC-D or L-Lys and the corresponding p-nitrophenyl ester.

D-Nitrophenyl nicotinate. To 9.85 g, 80 mmoles, nicotinic acid and 13.35 g, 96 mmoles p-nitrophenol in 250 ml DMF was added 16.5 g, 80 mmoles DCC with stirring in ice-bath. After 1 hour at 0° C. and 3 hours at room temperature the urea was filtered off and the product was precipitated by the addition of an equal volume of water. Filtration, drying in vacuo and recrystallization from i-PrOH gave 11.22 g, 57% of white needles, m.p. 172.5°–173° C. (24)

p-nitrophenyl isonicotinate was prepared, in the same manner 12 g, 61%, m.p. 139°–141° C., m.p. 137°–139° C. (18)

Also p-nitrophenyl 6-methylnicotinate was prepared in the same way. Yield from 70 mmoles 6-methylnicotinic acid: 6.0 g, 33% after recrystallization from MeOH. M.p. 156°–157° C. R$_f$(2% MeOH in CHCl$_3$)=0.57 NMR (CDCl$_3$): 2.7,s,3H,CH$_3$; 7.36,d,1H,py H$^5$;7.45,m,2H,H adjacent to the oxygen in the phenyl ring; 8.34,m,3H,H adjacent to the NO$_2$ group in the phenyl ring overlapping with py H$^4$; 9.27,d,1H,py H$^2$.

P-nitrophenyl picolinate. 4.92 g, 40 mmoles, picolinic acid and 5.84 g, 42 mmoles p-nitrophenol were suspended/dissolved in 200 ml CH$_2$Cl$_2$. Then 8.24 g 40 mmoles, DCC was added in 20 ml CH$_2$Cl$_2$ with vigorous stirring. Stirring was continued in room temperature for 17 hours. Then the mixture was filtered and the filter cake washed with 30–40 ml CH$_2$Cl$_2$. The raw product was first treated with 100 ml Et$_2$O with stirring in ice-bath and filtered. Recrystallization from 250 ul iPrOH gave 6.24 g, 63% product. M.p. 154°–6° C. (dec.). M.p. 145°–7° C. (18).

Pyrazinecarboxylic acid p-nitrophenylester. This compound was prepared using the same method as the previous compound. From 40 mmoles pyrazinecarboxylic acid and 44 mmoles p-nitrophenol was obtained 35.2 mmoles, 88%, ester. M.p. 180°–182° C. (dec.). R$_f$ (CHCl$_3$:MeOH=49:1)=

0.72. NMR (CDCl$_3$): 7.5,m and 8.37m,2H each, hydrogens adjacent to the oxygen and nitro group respectively in the phenol ring; 8.84,m,1H,pyrazine H$^5$; 8.9,d,1H,pyrazine H$^6$; 9.48,d,1H,pyrazine H$^3$.

BOC-NicLys. 2.5 g BOC-Lys (L or D) was suspended in 200 ml DMF with stirring. Then 1.1 equivalent of p-nitrophenyl nicotinate was added and the mixture stirred at room temperature for 36 hours. The mixture was then filtered and the filtrate evaporated to dryness at reduced pressure to yield a yellow oil. The residue was stirred with 2×50 ul Et$_2$O in ice-bath. The first Et$_2$O phase was decanted, the second was filtered off. Recrystallization from EtOAc/hexanes gave 2.05 g product, 58% (L-form). M.p. 138° C., lit. (17) 138°–141° C. L-form [a]$^{20}$D=−2.91° (MeOH), D-form [a]$^{20}$D=3.35° (MeOH).

L- and D-BOC-INicLys were prepared similarly by acylating 10 mmoles L or D BOC-Lys with p-nitrophenyl isonicotinate in 100 ml DMF, 40 hours, room temperature. The crude product was partitioned between 120 ml EtOAc and 50 ml H$_2$O. The EtOAc phase was extracted with 2×50 ml H$_2$O and 50 ml brine. The original aqueous phase was back-extracted with 30 ml EtOAc. The combined EtOAc phases were then dried (MgSO$_4$) and evaporated and the residue was treated with Et$_2$O and recrystallized as above to give 1.07 g, BOC- L-INicLys, 30.5%. The yield for the D compound was 1.26 g, 36%. NMR (Acetone d$_6$): 1.4,s,9H, t-butoxy group; 1.8–1.48,m,6H,B,y,d,—CH$_2$—; 3.44,t,2H, E-CH$_2$; 4.13,m,1H,a-CH; 7.77,m,2H,py H$^5$ and H$^3$; 8.70,m, 2H,py H$^2$ and H$^6$.

L- and D-BOC-PicLys. 1.23 g, 5 mmoles, of L- or D-BOC-Lys was stirred with 1.34 g, 5.5 mmoles, p-nitrophenyl picolinate in 60 ml DMF for 16 hours. After filtration and evaporation and product was purified by column chromatography on silica gel on a 4.5×32 cm column and the solvent system n-BuOH:py:HOAc:H$_2$O=30:10:3:12. The product after chromatography was dissolved in EtOAc and washed with H$_2$O, brine, dried and evaporated in vacuo. The yields were usually 60–70%. NHR (CDCl$_3$): 1.43,s,9H, t-butoxy group; 1.73–1.45,m,6H,B,y,d—CH$_2$; 3.47,m,2H,E-CH$_2$; 4.32,m,1H,a-CH; 7.43,m,1H,py H$^5$; 7.85,m,1H,py H$^4$; 8.2,m,1H,py H$^3$; 8.55,m,1H,py H$^6$.

L- and D-BOC-MNicLys. 10 mmoles BOC-Lys and 10.5 mmoles p-nitrophenyl 6-methylnicotinate were allowed to react in 150 ml DMF in the usual manner. After 27 hours filtration and evaporation yielded a yellow oil. Et$_2$O treatment (2×50 ml) gave 3.3 g product which was recrystallized from 50 ul 20% MeOH in EtoAc/hexane. Yield 2.87 g, 78.6% (L-form). R$_f$(n-BuOH:py:HOAc:H$_2$O=32:10:3:12)= 0.61. NMR(CDCl$_3$): 1.46,s,9H,t-butoxy group; 1.9–1.5,m, 6H,B,y,d—CH$_2$; 2.57,s,3H,py CH$_3$; 3.36,m,2H,E-CH$_2$; 4.11,m,1H,a-CH; 7.22,d,1H,py H$^5$; 8.08,m,1H,py H$^4$; 8.95, broad s,1H,py H$^2$.

L- and D-BOC-PzcLys. Using the method above was obtained from 7.7 mmoles pyrazine carboxylic acid p-nitrophenyl ester and 7 mmoles BOC-Lys, L or D, in 100 ml DMF about 6 mmoles product after recrystallization from iPrOH. R$_f$(n-BuOH:py:HOAc:H$_2$O=30:10:3:12)=0.47. NMR (CDCl$_3$): 1.45,s,9H,t-butoxy group; 1.9–1.48,m,6H, B,y,d—CH$_2$—; 3.51,m,2H,E-CH$_2$; 4.29,m,1H,a-CH; 8.52,q, 1H,pyrazine H$^5$; 8.77,d,1H,pyrazine H$^6$; 9.41,d,1H,pyrazine H$^3$.

BOC-L-Nicorn. This compound was prepared the usual way by reacting 7 mmoles p-nitrophenyl nicotinate with 5 mmoles BOC-Orn in 75 ml DMF for 36 hours. Evaporation and recrystallization from EtOAc gave 3.5 mmoles, 70%, Nicorn, m.p. 143°–144° C. R$_f$(n-BuOH:HOAc:H$_2$O=4:1:2) =0.70. NMR(CDCl$_3$): 1.45,s,9H,t-butoxy group; 7.46,m,1H, py H$^5$; 8.27,m,1H,py H$^4$; 8.69,m,1H,py H$^6$; 9.05,m,1H,py H$^2$.

BOC-D-trans-NACAla. 1.43 g, 5 mmoles, BOC-D-trans-3(4-aminocyclohexyl) alanine (provided by the Southwest Foundation for Biomedical Research) was stirred with 1.35 g, 5.5 mmoles, p-nitrophenyl nicotinate in 60 ml DMF for 120 hours in room temperature. The mixture was then filtered, evaporated, treated with Et$_2$O in ice bath and filtered again. Recrystallization was done by heating in 12 ml EtOH and adding 18 ml hot H$_2$O. This produced a clear solution from which crystals separated on cooling. This procedure was repeated twice. Yield: 0.98 g, 50%. Purity>95%. M.p.>220° C. NMR(DMSO d$_6$) : 1.46,s,9H,t-butoxy group; 1.9–1.48,m,11H,ring CH$_2$, ring CH in position 1 and B-CH$_2$; 3.72,m,1H,ring CH in position 4; 3.95,m,1H, a-CH; 7.48, m,1H,py H$^5$; 8.16,m,1H,py H$^4$; 8.67,m,1H,py H$^6$; 8.96,m, 1H,py H$^2$.

BOC-D-cis-NACAla. 5 mmoles BOC-D-cis-3(4-aminocyclohexyl)alanine (source: as above) and 5.5 mmoles p-nitrophenyl nicotinate were allowed to react in DMF as above. Reaction time: 25 hours. Purification was achieved by Et$_2$O treatment as above and silica gel chromatography on a 4.5×32 cm column using the solvent system CHCl$_3$:MeOH:py:HOAc=75:10:10:5. Yield 1.3 g, 61%, amorphous powder. R$_f$ (column system)=0.58. NMR (CDCl$_3$): 1.44,s,9H,t-butoxy group; 1.95–1.45,m,11H,ring CH$_2$, ring CH in position 1 and B-CH$_2$; 4.22,m,1H,a-CH; 4.35,m,1H,ring CH in position 4: 7.35, 8.24, 8.63 and 8.98, 1H each, assignments as previous compound.

BOC-IOrn(Z). This compound was prepared from BOC-Orn(Z) by reductive alkylation with acetone and H$_2$/Pd as described by Prasad et al. (23) followed by conversion to the Nd- z derivative with benzyl chloroformate in aqueous alkali (Schotten-Baumann conditions). Purification was achieved by chromatography on silica gel with CHCl$_3$/MeOH 85:15. R$_f$ (CHCl$_3$:MeOH:HOAC=85:15:3)=0.8. NMR(CHCl$_3$) 1.10,d,6H, isopropyl CH$_3$; 1.40,s,9H,t-butoxy group; 1.7–1.5,m,4H,B,y-CH$_2$; 3.09,m,2H, d-CH$_2$; 4.2,m,1H,a-CH; 5.10,s,2H,benzyl CH$_2$; 7.3,m,5H,aromatics.

BOC-CypLvs(Z). 2.04 g BOC-Lys(z) was dissolved in 8 ml of cyclopentanone and 32 ml H$_2$O containing 0.22 g NaOH. Hydrogenation was performed in the presence of 0.4 g 10% Pd/C at 50–60 psi in a Parr apparatus. After 4 hours the hydrogenation was interrupted and 2 ml 0.5M NaOH and 10 ul MeOH were added. The hydrogenation was then continued for 16 hours at 50–60 psi. Then filtration and evaporation. The residue was dissolved in 75 ml H$_2$O and the aqueous phase extracted with three times with Et$_2$O and once with hexane. The pH was then brought to 6–7 with HCl and the solution evaporated in rotary evaporator, bath temperature 40° C. The resulting product was then converted to the Z-derivative using benzyl chloroformate in aqueous NaOH (Schotten-Baumann conditions). Yield: 1.3 g, 58% overall. R$_f$ (n-BuOH:py:HOAC:H$_2$O—30:10:3:12)=0.69. Purity>95%. NMR (CDCl$_3$): 1.45,s,9H,t-butoxy group; 1.95–1.35,m,14H,ring CH$_2$+B,y,d-CH$_2$; 3.13,broad t,2H,E-CH$_2$; 4.34–4.05,m,2H,a-CH+ring CH; 5.13,s,2H,benzyl CH$_2$; 7.35,m,5H,aromatic protons.

BOC-Me$_2$Lys, D- and L-. These compounds were prepared by hydrogenolysis of the corresponding Z- or Cl-Z-derivatives in the presence of 37% formaldehyde essentially as described by L. Benoiton (22) for the N$^a$-acetyl analog. Purification was achieved by chromatography on silica gel with the solvent system n-BuOH:py:H$_2$O=2:2:1. The yields are 40–65% and the products are amorphous. NMR (CDCl$_3$): 1.41,s,9H,t-butoxy group; 1.9–1.5,m,6H,B,y, dCH$_2$; 2.6,s,6H,N(CH$_3$)$_2$; 2.8,m,2H,E-CH$_2$; 4.03,m,1H,a-CH.

BOC-D-AnGlu. 0.62 g, 3 mmoles, DCC was added to the ice-cooled solution of 1.10 g, 3 mmoles, BOC-D-glutamic acid a-benzylester and 0.39 g, 3 mmoles, p-anisidine in 25 ml CH$_2$Cl$_2$. The reaction mixture was stirred while warming up to room temperature and then another 17 hours. The dicyclohexylurea was then filtered off and CHCl$_3$ added to a total volume of 125 ml. This solution was extracted with 2×1N H$_2$SO$_4$, H$_2$O, saturated NaHCO$_3$, 2×H$_2$O and dried (MgSO$_4$). Evaporation and recrystallization from EtOH gave 0.99 g, 74% product, m.p. 129.5°–131° C. R$_f$(4% MeOH in CHCl$_3$)=0.53. This product was dissolved in 30 ml MeOH and 10 ml EtOH and hydrogenated in the presence of 0.3 g Pd/C at 50 psi for 2.5 hours. Filtration and evaporation gave a quantitative yield of BOC-D-AnGlu. Not crystalline. Purity>98%. NMR (CDCl$_3$): 1.45,s,9H,t-butoxy group; 2.35–1.95,m,2H,B-CH$_2$; 2.6–2.4,m,2H,y-CH$_2$; 3.76,s,3H, OCH$_3$; 4.3,m,1H,a-CH; 6.82 and 7.42, broad d, 2H each, aromatic protons.

BOC-Me$_3$Arg. First, N,N,N',S-tetramethylisothiourea was prepared by the procedure of Lecher and Hardy (19). B.p. (15 mm)=74° C., lit(above) 68° C. at 11 mm. BOC-Orn,9 mmoles, and teramethylisothiourea, 10 mmoles, were dissolved in 15 ml DMF and 2 ml triethylamine and incubated at 100° C. for 2 hours and at room temperature for 10 hours. Then the reaction mixture was evaporated to dryness and passed through a silica gel column eluted by iPrOH:triethylamine:H$_2$O=42:6:13. The white solid so obtained was dissolved in H$_2$O and the solution was acidified with 6N HCl and lyophilized to give 5.5 mmoles product. R$_f$ (column eluant)=0.50. NMR (D$_2$O): 1.42,s,9H, t-butoxy group, 2.80,m,1H,a-CH; 2.89,s,3H, CH$_3$ on guanidino group; 2.96,s,6H, (CH$_3$)$_2$N; 3.25,t,2H,d-CH$_2$; 1.50,m, 4H,B,y-CH$_2$.

BOC-Dpo. From 10 mmoles arginine hydrochloride and 1.72 g sodium hydrogen carbonate dissolved in 17 ml H$_2$O, 28.6 ml acetylacetone and 28.6 ml EtOH was obtained 7.5 mmoles Dpo following the procedure of F.-S. (20). The product was then converted to the corresponding BOC-derivative using di-t-butyl dicarbonate in 50% aqueous dioxane in the presence of sodium hydroxide. This reaction proceeds in essentially quantitative yield. R$_f$ (nBuOH:HOAc:H$_2$O=4:1:2)=0.63. NMR (CDCl$_3$): 1.45,s, 9H,t-butoxy group; 1.9–1.5,4H,B,y-CH$_2$; 2.33,s,6H,CH$_3$; 3.46,m,2H,d—CH$_2$; 4.24,m,1H,a-CH; 6.35,s,1H aromatic H. L- and D- forms react similarly.

BOC-D-Et$_2$Arg. This compound was prepared by the method of Nestor and Vickery, U.S. Pat. No. 4,530,920, Jul. 23, 1985. R$_f$ (nBuOH:HOAc:H$_2$O=4:1:2)=0.52.

SYNTHESIS OF THE PEPTIDES

The peptides of the present invention were synthesized by the solid phase method using a Beckman Model 990 Peptide Synthesizer. (1, 11) The benzhydrylamine hydrochloride resin (BHA-resin) was used as a solid support. The program of the synthesizer was divided into subprograms.

1. Deprotection: 1. CH$_2$Cl$_2$ (2×wash, 1 or 2 min); 2. 50% TFA in CH$_2$Cl$_2$ containing 0.1% indole (1×wash, 1 or 2 min); 3. 50% TFA in CH$_2$Cl$_2$ containing 0.1% indole (deprotection, 20 min); 4. CH$_2$Cl$_2$ (2×wash).

2. Neutralization: 1. CH$_2$Cl$_2$ (2×wash, 1 or 2 min); 2. DIEA (10% in CH$_2$Cl$_2$) (2×wash, 1 or 2 min); 3. DIEA (10% in CH$_2$Cl$_2$) (neutralization, 5 min); 4. CH$_2$Cl$_2$ (2×wash, 1 or 2 min).

3. DCC Coupling: 1. CH$_2$Cl$_2$ (2×wash, 1 or 2 min); 2. amino acid solution in CH$_2$Cl$_2$ (delivery, transfer, mix, 5 min); 3. DCC (10% in CH$_2$Cl$_2$, (delivery and mix, 180 min); 4. CH$_2$Cl$_2$ (2×wash, 1 or 2 min).

4. Active Ester Coupling: not used.

5. Final Wash: 1. CH$_2$Cl$_2$ (2×wash, 1 or 2 min); 2. i-PrOH (3×wash, 1 or 2 min); 3. DMF (3×wash, 1 or 2 min); 4. CH$_2$Cl$_2$ (3×wash, 1 or 2 min).

6. Wash after TFA Treatment: 1. CH$_2$Cl$_2$ (2×wash, 1 or 2 min); 2. i-PrOH (2×wash, 1 or 2 min); CH$_2$Cl$_2$ (3×wash, 1 or 2 min).

7. Acetylation: 1. CH$_2$Cl$_2$ (2×wash, 1 or 2 min); 2. 25% Ac$_2$O and Py in CH$_2$Cl$_2$ (1×wash, 1 or 2 min); 3. 25% Ac$_2$O and Py in CH$_2$ Cl$_2$ (acetylation, 20 min); 4. CH$_2$Cl$_2$ (2×wash, 1 or 2 min).

The first amino acid was attached to the resin by the program sequence 2-3-5. Before placing the resin into the reaction vessel, the resin was washed in a separatory funnel with 25 ul CH$_2$Cl$_2$/g resin to remove the fine particles. In all couplings, usually a 3–4 fold excess of the Boc-amino acid over the nitrogen content of the resin was used. This procedure generally resulted in a complete coupling reaction. If a positive ninhydrin color reaction was observed, a second coupling was performed (program sequence 3-5). Then, the resin was acetylated (program sequence 7-5).

The next amino acid was attached by the program sequence 1-6-2-3-5. For DCC coupling, all amino acids were dissolved in CH$_2$Cl$_2$. Acetylation of the amino acid residue in position 1 was performed using the program sequence 1-6-2-7-5. The volume of the solvents and the reagents used for the washing and the performing of the chemical reactions was about 10 ul/g resin.

CLEAVAGE OF THE PEPTIDES FROM THE RESIN

After all of the amino acids had been coupled, the peptide resin was dried overnight, in vacuo. The resin was then treated with double-distilled liquid hydrogen fluoride (10 ul/g resin) containing 10–25% distilled anisole or p-cresol for 1 hour at 0C. Then, the HF was evaporated under reduced pressure and the residue was dried overnight, in vacuo, by an oil pump. The mixture was then extracted several times with Et$_2$O (25 ul/g resin), then with aqueous. HOAc, 30%, 50%, 10%, and once with 25 ul distilled, deionized water. The combined aqueous solution was lyophilized to yield the crude peptide.

PURIFICATION AND CHARACTERIZATION OF THE PEPTIDES

Most peptides were purified by silica gel chromatography (1×60 cm column) using one of the solvent. systems nBuOH:HOAc:H$_2$O=4:1:2 or 4:1:5 upper phase or nBuOAc:nBuOH:HOAc:H$_2$O=2:8:2:3 followed by gel filtration over Sephadex G 25 with 6% HOAc as the eluant. In the case of unsatisfactory purity after this procedure the peptides were further purified by semipreparative HPLC using a Waters liquid chromatograph equipped with a 660 solvent programmer. A 1.2×25 cm m-Bondapak C$_{18}$ column was used with the solvent system A=0.1M NH$_4$OAc pH 5.0 and B=20% A+80% CH$_3$CN. Different gradients of increasing amounts of B in 15–25 minutes were employed to effect purification.

An alternate purification scheme has been gel filtration over Sephadex G-25 with 6% HOAc followed by chromatography over Sephadex LH 20 (2.5×100 cm) with the solvent system H$_2$O-nBuOH:HOAc:MeOH=90:10:10:8. If necessary, the latter procedure was repeated 1–2 times.

The purity of the peptides was assessed by thin layer chromatography on Merck silica gel plates in at least four different solvent systems. The spots were developed with the chlorine/o-tolidine reagent. The equipment was the one described above except that an analytical m-Bondapak C$_{18}$ column (3.9 mm×30 cm) was used.

Amino acid analyses were performed on a Beckman model 118 CL amino acid analyzer. Samples of about 0.5 ug were hydrolyzed in 6N hydrochloric acid in sealed glass tubes for 24 hours at 110° C. The residue was then evaporated and dissolved in citrate buffer, pH 2.2 and applied to the analyzer.

BIOASSAYS OF THE PEPTIDES AND DISCUSSION OF DATA

The antiovulatory activity, AOA, in rats was determined as described by Humphries et al. (12). Antiovulation assays were performed by counting, on estrus, the number of ova shed by 4-day cycling rats after a single sc injection of the LH-RH analogue in corn oil was administered between 12 and 12:30 p.m. on estrus. The control rats received 0.3 mL of the vehicle. The wheal test was performed by intradermally injecting 10 ug of peptide in 100 ul of saline into anaesthesized rats, measuring the ideally circular wheal response and calculating the area. The in vitro histamine release test was done as described by Karten et al. (4). A suspension of rat mast cells was added to increasing concentrations of peptide and the mixture was incubated for a few minutes followed by centrifugation to collect the histamine in the supernatant. A PIPES (piperazine-N,N'-bis[2-ethanesulfonic acid]) medium buffered at pH 7.4 containing NaCl 119 mM, KCl 5 mM, PIPES 25 mM, NaOH 40 mM, glucose 5.6 mM, CaCl$_2$ 1 mM, and 0.1% bovine serum albumin was used. This was designated as PIPES AC. Peptides were dissolved in double distilled H$_2$O at a concentration of 2 mg/ml and stored at −20° C. They were thawed just prior to testing, diluted in PIPES AC and prewarmed for five minutes at 37° C. Peptides studied were stable to heating at 56° C. for two hours, and to freezing and thawing.

Peritoneal cells were collected from male Sprague-Dawley rats weighing 200 to 250 gm and purchased from Harlan (Madison, Wis.). After euthanasia by CO$_2$, the peritoneal cavity was washed with 50 ml PIPES AC medium containing 20 units of heparin. Following centrifugation at 200×g for eight minutes at 4° C., cells were washed again and finally resuspended to a concentration of 8 to 24×10$^5$ total leukocytes/ml in PIPES AC. This suspension contained approximately 5–10% mast cells. Washed cells were used immediately after collection and were prewarmed for five minutes at 37° C. prior to pipetting 0.25 ml aliquots into 12×75 mm polystyrene tubes containing 0.25 ml of diluted peptide. Mixtures were incubated for 15 minutes at 37° C. and the reaction stopped by centrifugation at 400×g for 15 minutes at 4° C. The cell supernatants were assayed for histamine content by the automated fluorometric assay procedure. See, Siraganian, R. P., "An automated continuous flow system for the extraction and fluorometric analysis of histamine." Anal. Biochem. 57:383 (1974); and Siraganian, R. P. and Hook, W. A., "Histamine release and assay methods for the study of human allergy," In Manual of Clinical Immunology, 3rd ed., N. R. Rose, H. Friedman, and J. L. Fahey (Eds.), Amer. Soc. for Microbiology, Washington (1986) p. 808.

The results of these bioassays are presented in Table I and other Tables appended hereto.

Of the 57 peptides in Table I, 21 had an AOA of about 90% or more at a dosage of 1 ug in the present assay. Of the 37 peptides of Table 1 tested for histamine release in the rat mast cell assay, 10 had ED$_{50}$ values of 300 or more as compared to 0.17 for the standard compound [N-Ac-D-2-Nal$^1$,D-4-F-Phe$^2$,D-Trp$^3$,D-Arg$^6$]-LHRH. Nine additional analogs had ED$_{50}$ values ranging from 86 to 288, i.e. they do not release more histamine than clinically used "superagonists".

Of the thirty-seven peptides of Table 1 tested in the rat mast cell assay, seven (numbers 4, 23, 24, 43 (Antide), 44, 53, 55) had both an AOA of about 90% or more at 1 ug and an ED$_{50}$ value of about>86 ug/ml. This included the potent analog, No. 53, which had 100% AOA at 0.5 ug and 40% AOA at 0.25 ug. The ED$_{50}$ value for this analog was 93+28. It was thus demonstrated that high AOA with low histamine release could be found in the analogs of the present invention.

Structural features in common for these seven peptides are: 1) A D-Lys residue in position 6 which was acylated by the weakly basic nicotinic acid or analogs like picolinic and 6-methylnicotinic acid. 2) The corresponding acylated L-Lys residue or the natural Tyr in position 5. 3) The alkylated derivatives ILys or IOrn in position 8. 4) Arg is absent from the sequence.

Two examples of the influence of Arg on histamine release are the pairs 43,10 and 4,1. No. 43 (Antide) has the sequence N-Ac-D-2-Na$^1$,D-pClphe$^2$sub,D-3-Pal$^3$,Ser$^4$, NicLys$^5$,D-NicLys$^6$,Leu$^7$,ILys$^8$,Pro$^9$,D-Ala$^{10}$-NH$_2$. Its ED$_{50}$ value is>300. No. 10 is identical in sequence except that NicLys$^5$ is replaced by Arg$^5$. This caused the ED$_{50}$ value to decrease to 4.3±0.52. No. 4 has identical sequence as No. 43 except for Tyr in position 5. Its ED$_{50}$ value is 133±22. In No. 1, ILys$^8$ in this sequence is replaced by Arg$^8$ which caused the ED$_{50}$ value to decrease to 39.2±7. It thus seems that position 5 is more sensitive than position 8 for Arg substitution.

In position 8, the alkylated ILys and IOrn residues are superior to Lys and Orn, respectively, both with respect to AOA and histamine release (pairs 3,4 and 6,7). Whether ILYs$^8$ or IOrn$^8$ is best seems to be sequence dependent.

BIOLOGICAL ACTIVITIES

For the determination of duration of action, the antagonist was administered s.c. or orally to 26 days old female rats at a specific time before administration of the agonist, [D-Qal$^6$] -LHRH. The serum levels of rat luteinizing hormone (LH) and rat follicle stimulating hormone (FSH) were then measured 2 hours after the agonist administration by RIA. The oral administration was done through force-feeding with feeding tubes.

AOA AND HISTAMINE RELEASE DATA

Table IV shows data on AOA and histamine release for analogs containing acylated aminocyclohexylalanine residues. For the analogs with NicLys$^5$, D-NACAla$^6$, IV-1 and IV-2, (NACAla represents 3(4-nicotinoyl-aminocyclohexyl) alanine), analog 2 with cis-D-NACAla$^6$ is somewhat more active, 100% vs. 70% AOA at 1ug. Analogs IV-7 and IV-8 with NicLys$^5$, D-PzACAla$^6$ (PzACAla represents 3(4-pyrazinylcarbonylaminocyclohexyl)alanine) show the opposite order of activity. The trans residue has the higher AOA, 88% vs. 25% at 1ug.

Analogs IV-3 and IV-4 with PicLys[5], trans and cis PACAla[6] (PACAla represents 3(4-picolinoylaminocyclohexyl)alanine) are equipotent, 50 and 54% AOA at 0.5 ug, respectively, whereas in the case of PicLys[5], trans and cis PzACAla[6] the cis compound is more than twice as active. The former, analog IV-5 is about as potent as analogs IV-3 and IV-4 (44% at 0.5 ug) while the latter, analog 6, has 100%, 73%, and 29% AOA at 0.5, 0.25, and 0.125 ug, respectively. The high potency analog IV-6 is unique in comparison with the low activity of the structurally similar analog IV-8.

Analog IV-9 has cis-PzACAla[5], D-PicLys[6] and, although residues 5 and 6 are reversed, retained the high potency of analog IV-6, 90% and 67% at 0.5 and 0.25 ug, respectively.

As for histamine release, all analogs tested, in vitro, have lower $ED_{50}$ values than the parent compounds. The $ED_{50}$ values range from about 30 to about 60 compared to >300 and 93±11 for Antide and analog V-10. The tests for wheal response show a range from 99.5 to 129.6, which is similar to Antide (132.7) and analog V-10 (123.0). The lack of correlation between the two tests may primarily reflect assay variation.

In summary, for the analogs with NicLys[5], incorporation of aminocyclohexylalanine derivatives in position 6 resulted in substantial increase in, in vitro, histamine release and unchanged or lowered AOA. For the PicLys[5] analogs with the same substitutions there was lowering of AOA potency in all cases except one, where a considerable increase was observed. The combination PicLys[5] and cis-D-PzACAla[6] evidently possesses some beneficial structure. Histamine release for the PicLys[5] analogs was increased by 50–100%.

In Table V, are the results from substitutions in position 7 of analog V-10. This position allows some structural freedom although none of the peptides show higher AOA than analog V-10. Analogs V-12, V-14, and V-16 having Aile[7] (alloisoleucine), Val[7] and Abu[7] (2-aminobutyric acid), are equipotent with analog V-10. Analog V-16 with the straight chain Abu[7] is slightly more potent than analogs V-13 and V-15 with Nle[7] (norleucine) and Nval[7] (norvaline), respectively, which should more closely resemble the natural Leu[7].

For compound V-17 with the small Ala[7], the AOA decreased to 60% at 0.5 ug. Incorporation of Trp[7] which is the natural residue in chicken II, salmon and lamprey LHRH's (13–15), gave analog 18 with only 10% AOA at 0.5 ug. Trp[7] may be too large considering the size of the adjacent D-PicLys[6] and ILys[8].

The most interesting feature of Table V is the, in vitro, histamine release data. The three analogs with similar AOA potency as analog V-10 show markedly diminished histamine release. The $ED_{50}$ values for analogs V-12, V-14, and V-16 are >300, 213±30 and 273±27, respectively; i.e., a 2–3 fold decrease in histamine release is achieved by small changes in side chain structure. Also, the wheal response is diminished for all analogs compared to V-10.

It was noted earlier (1) that whether ILys or IOrn is the best substituent in position 8 is sequence dependant. To further investigate this aspect, the IOrn[8] analogs corresponding to some of the best peptides were synthesized and tested. The results in Table VI indicate that ILys[8] may be better. For two of the pairs, analogs VI-10, VI-19 and VI-12, VI-21, ILys[8] and IOrn[8] were about equivalent. For the other three pairs, the analogs with ILys[8] were more active, but the differences were not large. The largest difference was for the pair with Val[7], where the ILys[8]-analog VI-14 showed 90% AOA at 0.5 ug vs. 57% for the IOrn-analog VI-20.

Analog VI-19 was tested, in vitro, for histamine release. The $ED_{50}$ value is 42+3.1; i.e., the histamine release is 2-fold that of the analog with one more $CH_2$ unit. The wheal response did not change conspicuously except for the Aile[7] and IOrn[8] analog 21 which had the low value of 78.6±4.5 compared to the ILys analog 12 which had 97.9±2.9.

DURATION OF ACTION

Table VII shows the duration of action of Antide and two analogs. When Antide was injected 44 hours before 50 ng of [D-Qal[6]]-LHRH (Qal represents 3(3-quinolyl)alanine), a superagonist, at doses of 3, 10, and 30ug, significant reductions in serum LH were observed at the two higher doses. The LH decreased from 113±11 to 46±12 and 5±0.7 ng/ul. Serum FSH was also decreased, most significantly from about 3000 to about 300 ng/ul at 30 ug.

Analog VII-24, [Tyr[5]]-Antide, and analog IV-6 were similarly injected 24 hours before the agonist. Analog VII-24 showed high activity, reducing the LH level to 19±4, 3±0.4 and 0.3±0.03 ng/ul at doses of 3, 10, and 30 ug, respectively. The corresponding figures for analog IV-6 are 42±7, 15±3, and 3.4±2 ng/ul. This is interesting since in the antiovulatory assay analog IV-6 is considerably more potent, 73% at 0.25 ug vs. 45% at 0.5 ug. Perhaps, analog IV-6 is enzymatically degraded faster than analog VII-24. The long duration of action of these analogs s.c. may also be due to "depot" effects at the site of injection.

ORAL ACTIVITY

Table VIII shows the duration of action of Antide after oral administration. Forty-eight hours after administration of 100 or 300 ug dose levels of Antide, there were significantly reduced levels of LH which had been released by 5 ng of [D-Qal[6]]-LHRH s.c. Reductions from 21±3 to 4±0.8 and 8±2 ng/ul, respectively, were observed. The results are about the same in the −24 hour experiment (9±2 and 6±0.3 ng/ul). Antide appears to possess considerable resistance towards degrading enzymes. When Antide was given 2 hours before the agonist, a strong decrease in LH levels was observed. At a dose of 30 ug, a significant lowering of the LH level to 6±1 ng/ul was seen. At 100 and 300 ug, the levels were 1±0.3 and 0.4±0.4 ng/ul, i.e., very low levels. When 10 ng of agonist was used, the results are qualitatively very similar.

For comparison, the last three entries in Table VIII are from experiments with [N-Ac-D-pClPhe[1,2],D-Trp[3],D-Arg[6], D-Ala[10]]-LHRH, VIII-25, an analog that has been reported to have oral activity, (16). These data show that Antide is more active than VIII-25, since a dose of 30 ug given 2 hours before the agonist reduced the LH level from 44±4 to 22±4 ng/ul (p<0.01). The value for analog VIII-25 is 39±6 (NS). At 100 ug, the corresponding numbers are 7±3 (p<0.001) and 26±7 (p<0.05). The FSH levels were, in general, lowered when Antide was administered at −2 hours at 100 or 300 ug dose levels.

The results in Table IX show that there is no significant difference between administration of Antide in water or in corn oil.

Antide has also been tested orally in the antiovulatory assay (Table X). The AOA values at 300, 600, and 1200 ug dose levels are 18, 73, and 100% respectively. Expressed as rats ovulated/total rats, the numbers are 9/11, 3/11, and 0/11. For analog VIII-25, the numbers 9/11, 4/11, and 0/11 have been reported at dose levels of 500, 1000, and 2000 ug, respectively, (16). Antide was about twice as active as analog VIII-25.

Table XI shows a comparison of the oral activities of Antide and four analogs. One was as active as Antide, one was considerably less active and two were less active at low doses (30 and 100 ug) and about as active at 300 ug.

After a 15 ng s.c. dose of [D-Qal$^6$]-LHRH, the LH level rose-to 91±4.6 ng/ul. At oral dose levels of 30, 100, and 300 ug of Antide, reduced levels of LH of 75±3, 20±4, and 5±1 ng/ul, respectively, were recorded. Analog 4 with PicLys$^5$, and D-PACAla$^6$ showed no significant reduction of LH at 30 and 100 ug levels, but there was a reduction to 51±6 ng/ul at a 300 ug dose.

Analog V-12 with PicLys$^5$, D-PicLys$^6$, and Aile$^7$ and analog IV-6 with PicLys$^5$, cis-D-PzACAla$^6$ are less active than Antide at 30 and 100 ug, but were equally active at 300 ug. Both of these peptides were substantially more active than Antide in the s.c. antiovulatory assay.

Analog 26 was equipotent with Antide. This is not suprising since the only structural difference between these analogs is a pyrazine instead of a pyridine moiety in the N$^E$-acyl group of the D-Lys$^6$ residue.

Table XI and XII also shows results with Antide, for example, when 50 ng of the agonist was used. Comparison of these results with the data from the experiments using 15 ng of agonist shows a dose-response relationship which is expected from competitive antagonism. Using 15 ng of agonist, 100 and 300 ug of Antide reduced the LH level from 115±15 ng/ul to 20±4 and 5±1 ng/ul respectively, while in the experiments using 50 ng of agonist, 300 and 900 ug of Antide reduced the LH to the same level (19±3 and 5.3±1.2 ng/ul).

Table XIII shows the biological effects of Antide in a dispersed pituitary cell culture system.

The structures and biological activities of certain preferred LHRH analogs inhibiting more than 50% of ovulatory activity at a dose of 0.25 ug are shown in Table XIV.

It is proposed that Antide and other antagonists of the present invention may be utilized to induce a state of reversible medical castration that will be of value in the treatment of a rather large number of diseased states such as endometriosis, uterine fibroids and hormonal dependent cancers (prostate, breast). In some patients temporary inhibition of the function of the gonads with Antide, for example, while the patient is receiving chemotherapeutic agents and/or irradiation may prevent or minimize adverse effects of these agents on the gonads and thus help to preserve future fertility. Therapeutic examples would be irradiation during bone marrow transplantation, cervical carcinoma, metastatic thyroid and uterine carcinoma, possibly thyrotoxicosis, etc. during chemotherapy for disseminated lupus erythematosus and certain stages of organ transplantation. More physiological usages of the antagonists of the present invention such as Antide would be to inhibit fertility in both females and males.

More unique possible usages of Antide or other decapeptides of the present invention would be to modify sexual behavior during select disease states. Such disease states could involve patients with AIDS, the aggressive behavior of sex offenders in prisons or aggressive adolescents confined to corrective institutions. It is also possible is that high serum gonadotrophin levels of post-menopausal women may induce functional abnormalities in fat cells that cause weight gain or in bone cells that play a role in accelerated osteoporosis. These functional abnormalities could potentially be reduced with administration of Antide by inhibiting the high LH and/or FSH level in serum of post menopausal women.

Selective LH-RH antagonists mainly with charged amino acid substitutions in position 6 and/or 8 of the decapeptides probably stimulate histamine release by a direct effect on mast cells to release histamine while other LH-RH antagonists like Antide do not. It is thus proposed that the mast cell-stimulating antagonists applied locally to wounds of the skin may accelerate healing while non-histamine stimulating antagonists may prevent some of the allergic reactions which occur in humans.

To delay the onset of puberty in short stature children by administration of Antide with and without concommitant administration of GH or GH-releasing peptides is proposed as a unique method to enhance body height. The presence of gonadal hormones fuse the epiphysis of long bone and prevent their further elongation. This approach should extend and augment the use and effectiveness of GH and GH-releasing peptides.

The administration of LH-RH antagonists of the present invention acutely inhibits the function of the gonads within 24 hours. Continuous administration of LH-RH superagonists also inhibits the function of the gonads but this is only after several days of stimulating the gonads to hyperfunction. Such superagonist administration introduces a number of potential undesirable clinical problems in patients with prostate cancer, endometriosis, uterine fibroids as well as with sex offenders and those subjected to a temporary induction of medical castration. For these reasons it is proposed that LH-RH antagonists will be more desirable agents than LH-RH agonists for introducing a reversible state of medical castration. At the diagnostic level, such as differentiating the anatomic source of steroid secretion from the adrenal versus the ovary or to reveal the degree of calcium excretion dependency on gonadal steroid hormones, the rapid onset of inhibiting gonadal function with LH-RH antagonists makes them an unequivocally superior agent over LH-RH agonists. It is proposed that, in every clinical situation where LH-RH superagonists have been utilized to inhibit gonadal function, the LH-RH antagonists will be the agents of choice.

The references in the following list are incorporated by reference herein.

REFERENCES

1. Ljungqvist, A., Feng, D.-M., Tang, P.-F. L., Kubota, M., Okamoto, T., Zhang, Y., Bowers, C. Y., Hook, W. A. & Folkers K. (1987) *Biochem. BioPhys. Res. Commun.* 148 (2), 849–856.
2. Karten, M. D. & Rivier, J. E. (1986) *Endocr. Rev.* 7, 44–56.
3. Hook, W. A., Karten, M. & Siraganian, R. P. (1985) *Fed. Proc. Fed. Am. Soc. Exptl. Biol.* 44, 1323.
4. Karten, M. D., Hook, W. A., Siraganian, R. P., Coy, D. H., Folkers, K., Rivier, J. E. & Roeske, R. W. (1987) in *LHRH and its Analogs; Contraceptive and Therapeutic Applications Part 2* eds. Vickery, B. H. & Nestor, J. J., Jr., (MTP Press Ltd., Lancaster, England) pp. 179–190.
5. Rivier, J. E., Porter, J., Rivier, C. L., Perrin, M., Corrigan, A., Hook, W. A., Siraganian, R. P. & Vale, W. W. (1986) *J. Med. Chem.* 29, 1846–1851.
6. Roeske, R. W., Chaturvedi, N. C., Hrinyo-Pavlina, T., & Kowalczuk, M. (1987) in *LHRH and its Analogs; Contraceptive and Therapeutic Applications Part 2* eds. Vickery, B. H. & Nestor, J. J., Jr., (MTP Press Ltd., Lancaster, England) pp. 17–24.
7. Hocart, S. J., Nekola, M. V. & Coy, D. H. (1987) *J. Med. Chem.* 30, 739–743.
8. Nestor, J. J., Tahilramani, R., Ho, T. L., McRae, G. I. & Vickery, B. H. (1988) *J. Med. Chem.* 31, 65–72.

9. Bajusz, S., Kovacs, M., Gazdag, M., Bokser, L., Karashima, T., Csernus, V. J., Janaky, T., Guoth, J. & Schally, A. V. (1988) *Proc. Natl. Acad. Sci. USA* 85, 1637–1641.

10. Rivier, J., Kupryszewski, G., Varga, J., Porter, J., Rivier, C., Perrin, M., Hagler, A., Struthers, S., corrigan, A. & Vale, W. (1988) *J. Med. Chem.* 31, 677–682.

11. Folkers, K., Bowers, C. Y., Shieh, H.-M., Liu, Y.-Z., Xiao, S.-B., Tang, P.-F. L. & Chu, J.-Y. (1984) *Biochem. Biophys. Res. Commun.* 123 (3) 1221–1226.

12. Humphries, J., Wan, Y.-P., Folkers, K. & Bowers, C. Y. (1978) *J. Med. Chem.* 21(1), 120–123.

13. Miyamoto, K., Hasegawa, Y., Nomura, M., Igarashi, M., Kanagawa, K. & Matsuo, H. (1984) *Proc. Natl. Acad. Sci. USA* 81, 3874–3878.

14. Sherwood, N., Eiden, L., Brownstein, M., Spiess, J., Rivier, J., & Vale, W. (1983) *Proc. Natl. Acad. Sci. USA* 80, 2794–2798.

15. Sherwood, N. M., Sower, S. A., Marshak, D. R., Fraser, B. A. & Brownstein, M. J. (1986) J. Biol. Chem. 261, 4812–4819.

16. Nekola, M. V., Horvath, A., Ge, L.-J., Coy, D. H. & Schally, A. V. (1982) *Science* 218, 160–161.

17. Bernardi, et al., *J. Pharm. Pharmacol.* 19, 95 (1967).

18. Fife, T. H. and Przystas, T. J., *J. Am. Chem. Soc.* 107, 1041 (1985).

19. Lecher et al., U.S. Pat. No. 2,872,484, Feb. 3, 1959, *Chem. Abstr.* 53, 11238c.

20. Tjoeng et al., *Chem. Ber.* 108, 862 (1975).

21. Humphries et al., *J. Med. Chem.* 21(1), 120 (1978).

22. Benoiton, L., *Can. J., Chem.* 42, 2043 (1969).

23. Prasad et al., *J. Med. Chem.* 19, 492 (1976).

24. Zinner, H. and Fiedler, H., *Arch. Pharm.* 291(63), 330 (1958).

Changes may be made in the particular amino acid or derivatives and their assembly described herein or in the steps or the sequence of steps of the method described herein without departing from the concept and scope of the invention as defined in the following claims.

TABLE I

ANTAGONISTS OF LHRH BASED UPON
[( )$^1$, D-pClPhe$^2$, ( )$^3$, Ser$^4$, ( )$^5$,
( )$^6$, Leu$^7$, ( )$^8$, Pro$^9$, D-Ala$^{10}$]—NH$_2$

| | | Compound | | | | | AOA %/µg | | | Wheal Area | E$_D$50 |
|---|---|---|---|---|---|---|---|---|---|---|---|
| NO. | IBR # | ( )$^1$ | ( )$^3$ | ( )$^5$ | ( )$^6$ | ( )$^8$ | 0.5 | 1.0 | 2.0 | mm$^2$/10 µg | µg/ml |
| | | | | ANALOGS WITH D-NICLYS IN POSITION 6 | | | | | | | |
| 1. | 22396 | N—Ac-D-2-Nal | D-3-Pal | Tyr | D-NicLys | Arg | 60 | 100 | — | 85 | 39.2 ± 7 |
| 2. | 24753 | " | " | " | " | Me$_3$Arg | — | — | — | | 39.9 ± 7 |
| 3. | 24825 | " | " | " | " | Lys | — | 27 | — | 119.5 ± 3.2 | |
| 4. | 24315 | " | " | " | " | ILys | 45 | 89 | 100 | 79.0 ± 9.2 | 133 ± 22 |
| 5. | 24443 | " | " | " | " | Me$_2$Lys | — | 90 | 100 | 122.7 | 18.4 |
| 6. | 24748 | " | " | " | " | Orn | — | — | 67 | 129.4 ± 3.3 | 19.3 |
| 7. | 24756 | " | " | " | " | IOrn | 22 | 71 | — | 92.2 ± 2.9 | >300 |
| 8. | 24199 | " | " | Arg | " | Arg | 0 | 42 | — | 146.8 | |
| 9. | 24446 | " | D-Tyr | " | " | " | 33 | — | — | 113.2 ± 5.6 | 1.73 |
| 10. | 25335 | " | D-3-Pal | " | " | ILys | 43 | 17 | — | 196.9 ± 4.2 | 4.3 ± 0.52 |
| 11. | 24931 | " | " | Me$_3$Arg | " | " | — | — | 44 | 140 ± 7.0 | |
| 12. | 25506 | " | " | Dpo | " | " | 56 | — | — | 110 ± 3 | |
| 13. | 24543 | " | " | ILys | " | " | — | 89 | — | 132.7 ± 0 | 20.3 |
| 14. | 24545 | " | " | His | " | Arg | — | 89 | — | 139.7 ± 0 | |
| 15. | 24593 | " | " | 3-Pal | " | " | — | 100 | — | 146.4 ± 3.6 | |
| 16. | 25383 | " | " | " | " | ILys | — | 75 | — | 132.8 ± 6.0 | 86 ± 28* |
| 17. | 25384 | " | " | " | " | IOrn | — | 100 | — | 139.9 ± 7.2 | 55 ± 13* |
| 18. | 25144 | " | " | Ile | " | ILys | — | 82 | — | 147.7 ± 7.1 | 324 ± 20 |
| 19. | 25145 | " | " | " | " | IOrn | — | 55 | — | 116.5 ± 8.7 | 151 ± 75 |
| 20. | 25333 | " | " | NicOrn | " | " | — | 73 | — | 113.6 ± 10.9 | 57 ± 13 |
| 21. | 25509 | " | " | DMGLys | " | ILys | 20 | — | — | 110 ± 3 | 34 ± 1.1 |
| 22. | 25510 | " | " | PicLys | " | " | 64 | 100 | — | 116 ± 3.3 | 39 ± 1.0 |
| 23. | 25337 | N—Ac-D-pClPhe | " | Tyr | " | " | — | 100 | — | 139.7 ± 7.2 | 198 ± 33* |
| 24. | 25338 | N—Ac-D-Cl$_2$Phe | " | " | " | " | 0 | 89 | — | 103.9 ± 5.3 | 311 ± 65* |
| | | | | ANALOGS WITH NICLYS IN POSITION 5 | | | | | | | |
| 25. | 22495 | N—Ac-D-2-Nal | D-3-Pal | NicLys | D-3-Pal | Arg | 0 | — | — | 112 | |
| 26. | 24544 | " | " | " | D-His | " | — | 100 | — | 146.7 ± 3.6 | |
| 27. | 24754 | " | " | " | D-ILys | " | — | 56 | 73 | 196.9 ± 4.1 | |
| 28. | 25334 | " | " | " | D-Dpo | ILys | 40 | 100 | — | 165.2 ± 6.7 | 6.7 ± 2.2 |
| 29. | 25332 | " | " | " | D-BzLys | " | — | 50 | — | 119.6 ± 6.7 | >300 |
| 30. | 25507 | " | " | " | D-Et$_2$hArg | " | — | 67 | — | 123 ± 5.8 | |
| 31. | 25589 | " | " | " | D-PicLys | " | 36 | — | — | 120 ± 7 | 60 ± 1.4 |
| 32. | 25588 | " | " | " | D-AnGlu | " | — | 67 | — | 113 ± 7 | >300 |
| 33. | 25647 | " | " | " | trans-D-NACAla | " | — | 70 | — | 119.5 ± 3.2 | |
| 34. | 25648 | " | " | " | cis-D-NACAla | " | — | 100 | — | 113.6 ± 10.9 | 37 ± 1.1 |
| 35. | 25591 | " | " | " | D-Me$_2$Lys | " | — | 82 | — | 111 ± 2 | 262 ± 23 |
| 36. | 25649 | " | " | " | D-PzcLys | " | 78 | 92 | — | 122.2 ± 5.1 | |
| | | | | ANALOGS WITH NICLYS IN POSITION 8 | | | | | | | |
| 37. | 24749 | N—Ac-D-2-Nal | D-3-Pal | Tyr | D-Arg | NicLys | — | — | 88 | 136.3 ± 6.8 | 14.2 |
| 38. | 24771 | " | " | Arg | D-3-Pal | " | 0 | — | — | 99.0 ± 10.3 | |

TABLE I-continued

ANTAGONISTS OF LHRH BASED UPON [( )$^1$, D-pClPhe$^2$, ( )$^3$, Ser$^4$, ( )$^5$, ( )$^6$, Leu$^7$, ( )$^8$, Pro$^9$, D-Ala$^{10}$]—NH$_2$

| NO. | IBR # | ( )$^1$ | ( )$^3$ | ( )$^5$ | ( )$^6$ | ( )$^8$ | 0.25 | 0.5 | 1.0 | 2.0 | 10.0 | Wheal Area mm$^2$/10 µg | E$_D$50 µg/ml |
|---|---|---|---|---|---|---|---|---|---|---|---|---|---|
| 39. | 24824 | " | " | Tyr | D-ILys | " | — | — | 100 | | | 122.8 ± 5.8 | |

ANALOGS WITH NICLYS AND D-NICLYS IN POSITIONS 5, 6 OR IN POSITION 8, 6 OR IN POSITIONS 3, 6

| 40. | 24594 | N—Ac-D-2-Nal | D-3-Pal | NicLys | D-NicLys | Arg | 22 | 100 | — | | | 126.2 ± 8.8 | |
| 41. | 24987 | " | " | " | " | Me$_3$Arg | — | — | 100 | | | 150.9 ± 14.0 | |
| 42. | 25143 | " | " | " | " | Dpo | — | 18 | — | | | 113.6 ± 11.1 | <300 |
| 43. | 24542 | " | " | " | " | ILys | 36 | 100 | 100 | | | 132.7 ± 0 | 300 |
| 44. | 24933 | " | " | " | " | IOrn | 88 | 100 | — | | | 136.0 ± 3.4 | 206 ± 64 |
| 45. | 25078 | " | " | " | " | CypLys | — | 64 | — | | | 147.0 ± 7.1 | 171 ± 49 |
| 46. | 24540 | " | " | Tyr | " | NicLys | — | 0 | — | | | 82.6 ± 2.8 | 300 |
| 47. | 24745 | " | " | His | " | " | — | — | 18 | | | 136.3 ± 6.8 | |
| 48. | 24746 | " | " | " | ILys | " | — | 30 | — | | | 132.8 ± 5.9 | |
| 49. | 24597 | " | D-NicLys | Tyr | " | Arg | — | 89 | — | | | 101.0 ± 6.0 | |

MISCELLANEOUS ANALOGS

| | | Compounds | | | | | AOA %/µg | | | | | Wheal Area | E$_D$50 |
|---|---|---|---|---|---|---|---|---|---|---|---|---|---|
| NO. | IBR # | ( )$^1$ | ( )$^3$ | ( )$^5$ | ( )$^6$ | ( )$^8$ | 0.25 | 0.5 | 1.0 | 2.0 | 10.0 | mm$^2$/10 µg | µg/ml |
| 50. | 24596 | N—Ac-D-2-Nal | D-3-Pal | NicLys, | D-NicLys, | NicLys | — | — | 0 | — | — | 122.8 ± 5.7 | |
| 51. | 24934 | " | " | " | NicLys | Ilys | — | — | — | — | 8 | 123 ± 5.9 | >300 |
| 52. | 25146 | " | " | INicLys | D-INicLys | " | — | 63 | 91 | — | — | 140.3 ± 13.9 | 15 ± 8.2 |
| 53. | 25147 | " | " | PicLys | D-PicLys | " | 40 | 100 | 90 | — | — | 123.0 ± 0 | 93 ± 28 |
| 54. | 25385 | " | " | Arg | D-BzLys | " | — | — | 63 | — | — | 169.0 ± 7.7 | 8.7 ± 3* |
| 55. | 25386 | " | " | MNicLys | D-MNicLys | " | — | 56 | 100 | — | — | 126.1 ± 6.7 | >300* |
| 56. | 25508 | " | " | DMGLys | D-BzLys | " | — | — | 100 | — | — | 136.6.7 | 24 ± 0.3 |
| 57. | 25650 | " | " | PzcLys | D-PzcLys | " | — | 17 | — | — | — | 110.2 ± 8.1 | 288 ± 30 |

*In this test series, the standard compound had an E$_D$50 value of 0.46 instead of the usual 0.1–0.2.

TABLE II

ANALOGS WITH PicLys$^5$, D-PicLys$^6$

| | IBR # | Sequence | | | | | | | | |
|---|---|---|---|---|---|---|---|---|---|---|
| 58. | 26100 | N—Ac-D-Cl$_2$Phe, | D-pClPhe, | D-3-Pal, | Ser, | PicLys, | D-PicLys, | Leu, | ILys, | Pro, | D-Ala—NH$_2$ |
| 59. | 25807 | N—Ac-D-2-Nal | D-Cl$_2$Phe | " | " | " | " | " | " | " | " |
| 60. | 26364 | " | D-3-Pal | D-pClPhe | " | " | " | " | IOrn | " | " |
| 61. | 26119 | " | D-pClPhe | D-3-PzAla | " | " | " | " | " | " | " |
| 62. | 26177 | " | " | D-Trp | " | " | " | " | ILys | " | " |
| 63. | 25934 | " | " | D-3-Pal | " | " | " | Val | " | " | " |
| 64. | 26118 | " | " | " | " | " | " | " | IOrn | " | " |
| 65. | 25936 | " | " | " | " | " | " | Aile, | ILys | " | " |
| 66. | 26178 | " | " | " | " | " | " | " | IOrn | " | " |
| 67. | 25990 | " | " | " | " | " | " | Abu | ILys | " | " |
| 68. | 26179 | " | " | " | " | " | " | " | IOrn | " | " |
| 69. | 25935 | " | " | " | " | " | " | Trp | ILys | " | " |
| 70. | 25988 | " | " | " | " | " | " | Nle | " | " | " |
| 71. | 25989 | " | " | " | " | " | " | Nval | " | " | " |
| 72. | 26020 | " | " | " | " | " | " | Ile | " | " | " |
| 73. | 26099 | " | " | " | " | " | " | Ala | " | " | " |
| 74. | 26346 | " | " | " | " | " | " | Abu | Arg | " | " |
| 75. | 25937 | " | " | " | " | " | " | Leu | ILys | Pip | " |
| 76. | 26019 | " | " | " | " | " | " | " | " | Pro, D-Abu—NH$_2$ | |
| 77. | 25933 | " | " | " | " | " | " | " | Iom | " | D-Ala—NH$_2$ |

Analogs with PicLys$^5$.

| 78. | 26349 | N—Ac-D-2-Nal | D-pClPhe | D-TinGly | Ser | PicLys | c-D-PzACAla | Leu | ILys | Pro | D-Ala—NH$_2$ |
| 79. | 26324 | " | " | D-3-PxAla | " | " | " | " | " | " | " |
| 80. | 25897 | " | " | D-3-Pal | " | " | " | " | " | " | " |
| 81. | 26181 | " | " | " | " | " | " | " | IOrn | " | " |
| 82. | 26325 | " | " | " | " | " | " | Val | ILys | " | " |
| 83. | 26366 | " | " | " | " | " | " | Phe | " | " | " |
| 84. | 26347 | " | " | " | " | " | " | Leu | Arg | " | " |
| 85. | 26348 | " | " | " | " | " | " | " | ILys | " | D-Ser—NH$_2$ |
| 86. | 26383 | " | " | " | " | " | " | " | " | " | NHEt |
| 87. | 26323 | " | " | " | " | " | c-D-PmACAla | " | " | " | D-Ala—NH$_2$ |

TABLE II-continued

ANALOGS WITH PicLys⁵, D-PicLys⁶

| | IBR # | Sequence | | | | | | | | |
|---|---|---|---|---|---|---|---|---|---|---|
| | | | | | Analogs with D-PicLys⁶ | | | | | |
| 88. | 26180 | N—Ac-D-2-Nal | D-pClPhe | D-3-Pal | Ser | c-PzACAla | D-PicLys | Leu | ILys | Pro | D-Ala—NH₂ |
| 89. | 26381 | " | " | " | " | HOBLys | " | Abu | " | " | " |
| 90. | 26382 | " | " | " | " | Cit | " | " | " | " | " |
| 91. | 26363 | " | " | " | " | Tyr | " | Leu | IOrn | " | " |
| | | | | | Analogs with NicLys⁵. | | | | | |
| 92. | 25805 | N—Ac-D-2-Nal | D-pClPhe | D-3-Pal | Ser | NicLys | t-D-PzACAla | Leu | ILys | Pro | D-Ala—NH₂ |
| 93. | 25806 | " | " | " | " | " | c-D-PzACAla | " | " | " | " |
| 94. | 26345 | " | " | " | " | " | D-NicLys | NMeLeu | " | " | " |
| 95. | 25991 | " | " | " | " | " | D-PzcLys | Leu | IOrn | " | " |
| | | | | | Miscellaneous Substitutions in Positions 5 and 6. | | | | | |
| 96. | 25808 | N—Ac-D-2-Nal | D-pClPhe | D-3-Pal | Ser | MPicLys | D-M-PicLys | Leu | ILys | Pro | D-Ala—NH₂ |
| 97. | 26322 | " | " | " | " | PmcLys | D-PmcLys | " | " | " | " |
| 98. | 26326 | " | " | " | " | c-PzACAla | c-D-PzACAla | " | " | " | " |
| 99. | 26417 | " | " | " | " | " | D-3-PzAla | " | Arg | " | " |
| 100. | 26418 | " | " | " | " | Tyr | c-D-PzACAla | " | ILys | " | " |
| 101. | 26365 | " | " | " | " | " | " | " | " | " | D-Ser—NH₂ |
| | | | | | Analogs Being Synthesized at This Time. | | | | | |
| 102. | | N—Ac-D-2-Nal | D-pClPhe | D-3-Pal | Ser | Arg | D-3-Pal | Leu | Arg | Pro | Sar—NH₂ |
| 103. | | " | " | " | " | PicLys | c-D-PzACAla | " | ILys | " | " |
| 104. | | D-pGlu | " | D-Phe | " | Arg | D-3-Pal | " | Arg | " | D-Ala—NH₂ |
| 105. | | N—Ac-D-2-Nal | " | D-3-Pal | " | c-PzACAla | D-PicLys | Val | ILys | " | " |

TABLE III

Biological Data.
Analogs with PicLys⁵, D-PicLys⁶

| NO. | IBR | AOA/μg 0.25 | AOA/μg 0.5 | AOA/μg 1.0 | Wheal Area mm²/10 μg | In Vitro Histamine Release ED₅₀ μg/ml ± SEM |
|---|---|---|---|---|---|---|
| 58. | 26100 | — | 38 | — | 116.2 ± 3.7 | |
| 59. | 25807 | — | 64 | 90 | 139.8 ± 7.1 | |
| 60. | 26364 | 12 | — | — | 116.2 ± 5.5 | |
| 61. | 26119 | — | 75 | — | 103.9 ± 3.4 | |
| 62. | 26177 | — | 20 | — | 71.0 ± 4.3 | |
| 63. | 25934 | 43 | 90 | 100 | 97.9 ± 2.9 | 213 ± 30 |
| 64. | 26118 | — | 57 | — | 119.6 ± 6.6 | |
| 65. | 25936 | 43 | 89 | — | 97.9 ± 2.9 | >300 |
| 66. | 26178 | — | 82 | — | 78.6 ± 4.5 | |
| 67. | 25990 | 36 | 100 | — | 91.0 ± 5.4 | 273 ± 27 |
| 68. | 26179 | — | 80 | — | 101.5 ± 9.3 | |
| 69. | 25935 | — | 10 | — | 78.5 ± 0 | |
| 70. | 25988 | 20 | 77 | — | 107.0 ± 6.0 | |
| 71. | 25989 | 10 | 100 | — | 95.3 ± 6.0 | |
| 72. | 26020 | 0 | — | — | 110.7 ± 2.3 | |
| 73. | 26099 | — | 60 | — | 103.9 ± 3.7 | |
| 74. | 26346 | 50 | 88 | — | 113.2 ± 5.4 | |
| 75. | 25937 | — | 0 | 100 | 95.0 ± 0 | |
| 76. | 26019 | — | 78 | — | 109.9 ± 3.0 | |
| 77. | 25933 | 50 | 90 | 100 | 113.0 ± 0 | |
| | | | | | Analogs With PicLys⁵ | |
| 78. | 26349 | 0 | — | — | 84.6 ± 3.9 | |
| 79. | 26324 | 22 | 100 | — | 127.8 ± 4.9 | |
| 80. | 25897 | 73 | 100 | — | 122.8 ± 5.7 | 28 ± 7.5 |
| 81. | 26181 | 50 | 100 | — | 101.6 ± 2.2 | |
| 82. | 26325 | 73 | 100 | — | 127.8 ± 4.9 | |
| 83. | 26366 | 0 | — | — | 116.2 ± 3.2 | |
| 84. | 26347 | 14 | — | — | 119.6 ± 8.5 | |
| 85. | 26348 | 22 | — | — | 122.8 ± 5.7 | |
| 86. | 26383 | 25 | — | — | 119.6 ± 6.6 | |
| 87. | 26323 | — | 9 | — | 120.4 ± 4.7 | |
| | | | | | Analogs With D-PicLys⁶ | |
| 88. | 26180 | 67 | 90 | — | 99.5 ± 4.5 | |
| 89. | 26381 | 11 | — | — | 95.1 ± 5.0 | |
| 90. | 26382 | 11 | — | — | 89.5 ± 5.5 | |
| 91. | 26363 | 0 | — | — | 113.2 ± 5.5 | |
| | | | | | Analogs With NicLys⁵ | |
| 92. | 25805 | — | 67 | 88 | 129.6 ± 8.8 | |
| 93. | 25806 | — | — | 25 | 101.7 ± 5.0 | |
| 94. | 26345 | 10 | — | — | 110.5 ± 11.4 | |
| 95. | 25991 | — | 44 | — | 104.3 ± 10.5 | |
| | | | | | Analogs With Miscellaneous Substituents in Positions 5 and 6. | |
| 96. | 25808 | — | 67 | 91 | 106.2 ± 4.3 | |
| 97. | 26322 | 0 | — | — | 130.2 ± 2.5 | |
| 98. | 26326 | 57 | 100 | — | 115.5 ± 2.4 | |
| 99. | 26417 | 22 | — | — | 133.2 ± 11.8 | |
| 100. | 26418 | 22 | — | — | 95.0 ± 0 | |
| 101. | 26365 | 0 | — | — | 129.4 ± 3.3 | |

TABLE IV

Biological Data for [N—Ac-D-2-Nal$^1$, D-pClPhe$^2$, D-3-Pal$^3$, X$^5$, Y$^6$, ILys$^8$, D-Ala$^{10}$ ]-LHRH Analogs

| NO. | X | Y | AOA %/µg 0.125 | 0.25 | 0.5 | 1.0 | In Vitro Histamine Release ED$_{50}$ µg/ml ± SEM | Wheal Area mm$^2$/10 µg |
|---|---|---|---|---|---|---|---|---|
| IV-1. | NicLys | trans-D-NACAla | — | — | — | 70 | | 119.5 ± 3.2 |
| IV-2. | " | cis-D-NACAla | — | — | 50 | 100 | 37 ± 1.1 | 101.8 ± 4.3 |
| IV-3. | PicLys | trans-D-PACAla | — | — | 50 | — | 64 ± 5.4 | 101.0 ± 3.0 |
| IV-4. | " | cis-D-PACAla | — | — | 54 | — | 41 ± 5.4 | 123.0 ± 5.0 |
| IV-5. | " | trans-D-PzACAla | — | — | 44 | — | 39 ± 4.4 | 106.3 ± 4.3 |
| IV-6. | " | cis-D-PzACAla | 29 | 73 | 100 | — | 28 ± 7.5 | 122.8 ± 5.7 |
| IV-7. | NicLys | trans-D-PzACAla | — | — | 67 | 88 | | 129.6 ± 8.8 |
| IV-8. | " | cis-D-PzACAla | — | — | — | 25 | | 101.7 ± 5.0 |
| IV-9. | cis-PzACAla | D-PicLys | — | 67 | 90 | — | | 99.5 ± 4.5 |

TABLE V

Biological Data for [N—Ac-D-2-Nal$^1$, D-pClPhe$^2$, D-3-Pal$^3$, PicLys$^5$, D-PicLys$^6$, X$^7$, ILys$^8$, D-Ala$^{10}$ ]-LHRH Analogs.

| NO. | X | AOA %/µg 0.25 | 0.5 | 1.0 | In Vitro Histamine Release ED$_{50}$ µg/ml ± SEM | Wheal Area mm$^2$/10 µg |
|---|---|---|---|---|---|---|
| V-10.* | Leu | 40 | 100 | 90 | 93 ± 11 | 123 ± 0 |
| V-11. | Ile | 0 | — | — | | 110.7 ± 2.3 |
| V-12. | AIle | 43 | 89 | — | >300 | 97.9 ± 2.9 |
| V-13. | Nle | 20 | 77 | — | | 107.0 ± 6.0 |
| V-14. | Val | 43 | 90 | 100 | 213 ± 30 | 97.9 ± 2.9 |
| V-15. | NVal | 10 | 100 | — | | 95.3 ± 6.0 |
| V-16. | Abu | 36 | 100 | — | 273 ± 27 | 91.0 ± 5.4 |
| V-17. | Ala | — | 60 | — | | 103.9 ± 3.7 |
| V-18. | Trp | — | 10 | — | | 78.5 ± 0 |

*From Reference 1

TABLE VI

Biological Data for [N—Ac-D-2-Nal$^1$, D-pClPhe$^2$, D-3-Pal$^3$, PicLys$^5$, X$^6$, Y$^7$, Z$^8$, D-Ala$^{10}$]-LHRH Analogs

| NO. | X | Y | Z | AOA%/µg 0.25 | 0.5 | 1.0 | In Vitro Histamine Release ED$_{50}$ µg/ml ± SEM | Wheal Area mm$^2$/10 µg |
|---|---|---|---|---|---|---|---|---|
| VI-10.* | D-PicLys | Leu | ILys | 40 | 100 | 90 | 93 ± 11 | 123 ± 0 |
| VI-19. | " | " | IOrn | 50 | 90 | 100 | 42 ± 3.1 | 113.0 ± 0 |
| VI-14. | " | Val | Ilys | 43 | 90 | 100 | 213 ± 30 | 97.9 ± 2.9 |
| VI-20. | " | " | IOrn | — | 57 | — | | 119.6 ± 6.6 |
| VI-12. | " | AIle | ILys | 43 | 89 | — | >300 | 97.9 ± 2.9 |
| VI-21 | " | " | IOrn | — | 82 | — | | 78.6 ± 4.5 |
| VI-16. | " | Abu | ILys | 36 | 100 | — | 273 ± 27 | 91.0 ± 5.4 |
| VI-22. | " | " | IOrn | — | 80 | — | | 101.5 ± 9.3 |
| VI-6. | cis-D-PzACAla | Leu | ILys | 73 | 100 | — | 28 ± 7.5 | 122.8 ± 5.7 |
| VI-23. | " | " | IOrn | 50 | 100 | — | | 101.6 ± 2.2 |

*From Reference 1

TABLE VII

Duration of Action of Antide and Two Analogs Subcutaneously* Administered.

|  |  |  | 0 Time ng sc | +2 hrs | | | |
|---|---|---|---|---|---|---|---|
| Analog | Injection Time | Dose µg | [D-3-Qal⁶]- LHRH | LH ng/ml ± SEM | p value | FSH ng/ml ± SEM | p value |
| — | — | — | — | 0.4 ± 0.03 | <.001 | 143 ± 10 | <.001 |
| — | — | — | 50 | 113 ± 11 | — | 2899 ± 387 | — |
| Antide | −44 hr | 3 | 50 | 90 ± 5 | NS | 2497 ± 155 | NS |
| " | " | 10 | 50 | 46 ± 12 | <.001 | 1413 ± 230 | <.01 |
| " | " | 30 | 50 | 5 ± 0.7 | <.001 | 311 ± 34 | <.001 |
| VII-24† | −24 hr | 3 | 50 | 19 ± 4 | <.001 | 719 ± 123 | <.001 |
| " | " | 10 | 50 | 3 ± 0.4 | <.001 | 289 ± 30 | <.001 |
| " | " | 30 | 50 | 0.3 ± 0.03 | <.001 | 147 ± 10 | <.001 |
| IV-6(25897) | " | 1 | 50 | 91 ± 19 | NS | 2020 ± 295 | NS |
| " | " | 3 | 50 | 42 ± 7 | <.001 | 1298 ± 275 | <.01 |
| " | " | 10 | 50 | 15 ± 3 | <.001 | 624 ± 84 | <.001 |
| " | " | 30 | 50 | 3.4 ± 2 | <.001 | 273 ± 89 | <.001 |

*Mean of 6 ± SEM
†[Tyr⁵]-Antride

TABLE VIII

Duration of Action of Orally Administered Antide and Comparison with [N—Ac-D-pClPhe¹,², D-Trp³, D-Arg⁶, D-Ala¹⁰]-LHRH (25).*

|  | Time of adm.†† hr | Dose µg | 0 Time Agonist† Dose (sc) ng | +2 hours Serum LH ng/ml ± SEM | p value | FSH ng/ml ± SEM | p value |
|---|---|---|---|---|---|---|---|
| Antagonist |  |  |  |  |  |  |  |
| — | — | — | — | 3 ± 1 | <.001 | 298 ± 20 | <.001 |
| — | — | — | 5 | 21 ± 3 | — | 796 ± 102 | — |
| Antide | −48 | 100 | 5 | 4 ± 0.8 | <.001 | 481 ± 27 | <.02 |
| " | −48 | 300 | 5 | 8 ± 2 | <.01 | 600 ± 72 | NS |
| " | −24 | 100 | 5 | 9 ± 2 | <.01 | 596 ± 50 | NS |
| " | −24 | 300 | 5 | 6 ± 0.3 | <.001 | 462 ± 54 | <.02 |
| " | −2 | 10 | 5 | 19 ± 4 | NS | 588 ± 70 | NS |
| " | −2 | 30 | 5 | 6 ± 1 | <.001 | 573 ± 67 | NS |
| " | −2 | 100 | 5 | 1 ± 0.3 | <.001 | 320 ± 48 | <.01 |
| " | −2 | 300 | 5 | 0.4 ± 0.4 | <.001 | 327 ± 63 | <.01 |
| — | — | — | — | 3 ± 1 | <.001 | 298 ± 20 | <.001 |
| — | — | — | 10 | 44 ± 4 | — | 1488 ± 168 | — |
| Antide | −48 | 100 | 10 | 18 ± 2 | <.001 | 792 ± 110 | <.01 |
| " | −48 | 300 | 10 | 25 ± 3 | <.01 | 1021 ± 202 | NS |
| " | −24 | 100 | 10 | 24 ± 6 | <.02 | 1008 ± 285 | NS |
| " | −24 | 100 | 10 | 25 ± 3 | <.01 | 1119 ± 71 | NS |
| " | −2 | 10 | 10 | 51 ± 8 | NS | 1729 ± 243 | NS |
| " | −2 | 30 | 10 | 22 ± 4 | <.01 | 1051 ± 141 | NS |
| " | −2 | 100 | 10 | 7 ± 3 | <.001 | 548 ± 83 | <.001 |
| " | −2 | 300 | 10 | 0.5 ± .06 | <.001 | 251 ± 24 | <.001 |
| VIII-25 | −2 | 10 | 10 | 59 ± 11 | NS | 1794 ± 329 | NS |
| " | −2 | 30 | 10 | 39 ± 6 | NS | 1470 ± 190 | NS |
| " | −2 | 100 | 10 | 26 ± 7 | <.05 | 1161 ± 277 | NS |

*Kindly provided by Dr. David Coy
†[D-Qal⁶]-LHRH
††Administered in water

TABLE IX

Oral Activity of Antide. Dependence on Vehicle.

|  | −2 hrs | 0 Time | +2 hrs | | | |
|---|---|---|---|---|---|---|
| Vehicle | Antagonist Dose µg oral | Agonist Dose ng sc | LH ng/ml ± SEM | p value | FSH ng/ml ± SEM | p value |
| water | — | — | 1.1 ± 0.1 | <.001 | 243 ± 35 | <.001 |
| " | — | 50 | 148 ± 9 | — | 3041 ± 238 | — |
| " | 100 | 50 | 44 ± 5 | <.001 | 1372 ± 84 | <.001 |
| " | 300 | 50 | 20 ± 4 | <.001 | 936 ± 150 | <.001 |

TABLE IX-continued

Oral Activity of Antide. Dependence on Vehicle.

| | −2 hrs | 0 Time | +2 hrs | | | |
|---|---|---|---|---|---|---|
| Vehicle | Antagonist Dose μg oral | Agonist Dose ng sc | LH ng/ml ± SEM | p value | FSH ng/ml ± SEM | p value |
| " | 900* | 50 | 6.3 ± 3 | <.001 | 374 ± 80 | <.001 |
| corn oil | — | — | 0.8 ± 0.6 | <.001 | 138 ± 6 | <.001 |
| " | — | 50 | 115 ± 8 | — | 2935 ± 133 | — |
| " | 100 | 50 | 72 ± 12 | <.01 | 2148 ± 234 | <.02 |
| " | 300 | 50 | 20 ± 4 | <.001 | 792 ± 137 | <.001 |
| " | 900 | 50 | 7 ± 2 | <.001 | 599 ± 59 | <.001 |

Design: −2 hrs - Antagonist
0 time - [D-3-Qal$^6$]-LHRH
+2 hrs - Sacrifice
26 day old female rates. Mean of 6 ± SEM
*Diluted 1:1 with 10 mM HOAC:Water (slightly cloudy) 0.1 ml orally, other concentration diluted with water

TABLE X

Oral Activity of Antide in the Antiovulatory Assay.*

| Oral Dose μg | AOA % Inhibition (# Ovulated/# Rats) |
|---|---|
| — | 0 (6/6) |
| 300 | 18 (9/11) |
| 600 | 73 (3/11) |
| 1200 | 100 (0/11) |

*in 10 mM acetic acid:water (1:1)

TABLE XI

Oral Activity of Antide and Some Analogs.

| | | 0 Time | +2 hrs | | | |
|---|---|---|---|---|---|---|
| Antagonist | −2 hrs Dose μg oral | Agonist Dose ng sc | LH ng/ml ± SEM | p value | FSH ng/ml ± SEM | p value |
| | — | — | 3.4 ± 2.2 | <.001 | 271 ± 56 | <.001 |
| | — | 15 | 91 ± 4.6 | — | 2491 ± 146 | — |
| Antide | 30 | 15 | 75 ± 3 | <.02 | 1718 ± 223 | <.02 |
| " | 100 | 15 | 20 ± 4 | <.001 | 738 ± 89 | <.001 |
| " | 300 | 15 | 5 ± 1 | <.001 | 472 ± 26 | <.001 |
| 4 | 30 | 15 | 79 ± 9 | NS | 1831 ± 249 | <.05 |
| " | 100 | 15 | 76 ± 6 | NS | 2175 ± 211 | NS |
| " | 300 | 15 | 51 ± 6 | <.001 | 1404 ± 117 | <.001 |
| 12 | 30 | 15 | 71 ± 9 | NS | 1965 ± 256 | NS |
| " | 100 | 15 | 54 ± 10 | <.01 | 1031 ± 195 | <.001 |
| " | 300 | 15 | 6 ± 1.1 | <.001 | 514 ± 54 | <.001 |
| 26* | 30 | 15 | 75 ± 9 | NS | 2438 ± 207 | NS |
| " | 100 | 15 | 19 ± 3 | <.001 | 845 ± 149 | <.001 |
| " | 300 | 15 | 6 ± 1.4 | <.001 | 431 ± 22 | <.001 |
| 6 | 30 | 15 | 77 ± 12 | NS | 1761 ± 191 | <.01 |
| " | 100 | 15 | 59 ± 12 | <.05 | 1782 ± 388 | NS |
| " | 300 | 15 | 6.3 ± 1.4 | <.001 | 467 ± 43 | <.001 |
| | — | 50 | 115 ± 15 | — | 2372 ± 126 | — |
| Antide | 30 | 50 | 93 ± 7 | NS | 2262 ± 55 | NS |
| " | 100 | 50 | 49 ± 7 | <.001 | 1345 ± 199 | <.001 |
| " | 300 | 50 | 19 ± 3 | <.001 | 630 ± 40 | <.001 |
| " | 900 | 50 | 5.3 ± 1.2 | <.001 | 450 ± 48 | <.001 |

Design: −2 hrs - Antagonist
0 Time - [D-3-Qal$^6$]-LHRH
+2 hrs - Sacrifice
26 day old female rats. Mean of 6 ± SEM
Vehicle - 10 mM HOAC:Water (1:1) 0.1 ml
*[D-N$^\alpha$-pyrazinylcarbonyllysyl$^6$]-Antide

TABLE XII

ORAL ACTIVITY OF ANTIDE
At Various Time Schedules and Doses of a LH-RH Superagonist
[NAcD2Nal¹,DpClPhe²,D3Pal³,NicLys⁵,DNicLys⁶,ILys⁸,DAla¹⁰]LHRH

| Antagonist | | Agonist* | | | | |
|---|---|---|---|---|---|---|
| Time adm. (oral) hr | Dosage µg | Dose (sc) 0 TIME | LH ng/ml ± SEM | p value +2 HOURS | FSH ng/ml ± SEM | p value |
| — | — | — | 3 ± 1 | <.001 | 298 ± 20 | <.001 |
| — | — | 5 ng | 21 ± 3 | — | 796 ± 120 | — |
| −48 | 100 | 5 ng | 4 ± 0.8 | <.001 | 481 ± 27 | <.02 |
| −48 | 300 | 5 ng | 8 ± 2 | <.01 | 600 ± 72 | NS |
| −24 | 100 | 5 ng | 9 ± 2 | <.01 | 596 ± 50 | NS |
| −24 | 300 | 5 ng | 6 ± 0.3 | <.001 | 462 ± 54 | <.02 |
| −2 | 10 | 5 ng | 19 ± 4 | NS | 588 ± 70 | NS |
| −2 | 30 | 5 ng | 6 ± 1 | <.001 | 573 ± 67 | NS |
| −2 | 100 | 5 ng | 1 ± 0.3 | <.001 | 320 ± 48 | <.01 |
| −2 | 300 | 5 ng | 0.4 ± 0.4 | <.001 | 327 ± 63 | <.01 |
| — | — | — | 3 ± 1 | <.001 | 298 ± 20 | <.001 |
| — | — | 10 ng | 44 ± 4 | — | 1488 ± 168 | — |
| −48 | 100 | 10 ng | 18 ± 2 | <.001 | 792 ± 110 | <.01 |
| −48 | 300 | 10 ng | 25 ± 3 | <.01 | 1021 ± 202 | NS |
| −24 | 100 | 10 ng | 24 ± 6 | <.02 | 1008 ± 285 | NS |
| −24 | 300 | 10 ng | 25 ± 3 | <.01 | 1119 ± 71 | NS |
| −2 | 10 | 10 ng | 51 ± 8 | NS | 1729 ± 243 | NS |
| −2 | 30 | 10 ng | 22 ± 4 | <.01 | 1051 ± 141 | NS |
| −2 | 100 | 10 ng | 7 ± 3 | <.001 | 548 ± 83 | <.001 |
| −2 | 300 | 10 ng | 0.5 ± .06 | <.001 | 251 ± 24 | <.001 |
| −2 | 10** | 10 ng | 59 ± 11 | NS | 1794 ± 329 | NS |
| −2 | 30 | 10 ng | 39 ± 6 | NS | 1470 ± 190 | NS |
| −2 | 100 | 10 ng | 26 ± 7 | <.05 | 1161 ± 277 | NS |

*24270 [D3Qal⁶]-LHRH
**AH-195-3 NAcDpClPhe¹,²,DTrp³,DAla¹⁰-LHRH (Dr. David Coy)
mean of 6 ± SEM

TABLE XIII

Effect of Antide in the Dispersed Pituitary Cell Culture Assay

| Peptide | Dose nM | LHRH nM | RLH ng/ml ± SEM | p value | IDR₅₀ | FSH ng/ml ± SEM | p value | IDR₅₀ |
|---|---|---|---|---|---|---|---|---|
| Control | — | — | 10 ± 0.4 | — | | 196 ± 23 | — | |
| LHRH | — | 0.1 | 40 ± 7 | <.05 | | 221 ± 18 | NS | |
| | — | 0.3 | 80 ± 1 | <.001 | | 562 ± 48 | ≅.02 | |
| | — | 1.0 | 118 ± | NA | | 802 ± | NA | |
| | — | 3.0 | 150 ± 1 | <.001 | — | 646 ± 123 | NS | — |
| | — | 10.0 | 141 ± 4 | <.001 | | 602 ± 26 | <.01 | |
| | — | 30.0 | 152 ± 7 | <.01 | | 557 ± 15 | <.01 | |
| 139-95-20 | 0.01 | 3.0 | 118 ± 11 | NS* | 0.26:1 | 546 ± 93 | NS* | 0.52:1 |
| | 0.03 | 3.0 | 117 ± 10 | NS | | 499 ± 26 | NS | |
| | 0.1 | 3.0 | 116 ± 7 | <.05 | | 472 ± 59 | NS | |
| | 0.3 | 3.0 | 107 ± 11 | NS | | 617 ± 73 | NS | |
| | 1.0 | 3.0 | 80 ± 2 | <.001 | | 481 ± 17 | NS | |
| | 3.0 | 3.0 | 34 ± 2 | <.001 | | 233 ± 38 | NS | |
| | 10.0 | 3.0 | 11 ± 1 | <.001 | | 165 ± 21 | NS | |

*p values vs 3 nM of LHRH
139-95-20 [NAcD2Nal¹,DpClPhe²,D3Pal³,NicLys⁵,DNicLys⁶,ILys⁸,DAla¹⁰]LHRH

TABLE XIV

LHRH analogs with 50% or more AOA at 0.25 ug

| IBR # | Sequence | | | | | | | | | | AOA/ 0.25 | Wheal area | ED |
|---|---|---|---|---|---|---|---|---|---|---|---|---|---|
| 25897 | N-Ac-D-2-Nal, | DpClPhe, | D-3-Pal, | Ser, | PicLys, | c-D-PzACAla, | Leu, | ILys, | Pro, | D-Ala-NH₂ | 73 | 122.8 ± 5.7 | 28⁵⁰ ± 7.5 |
| 26325 | N-Ac-D-2-Nal, | DpClPhe, | D-3-Pal, | Ser, | PicLys, | c-D-PzACAla, | Val | ILys, | Pro, | D-Ala-NH₂ | 73 | 127.8 ± 4.9 | |
| 26180 | N-Ac-D-2-Nal, | DpClPhe, | D-3-Pal, | Ser, | c-PzACAla, | D-PicLys | Leu | ILys, | Pro, | D-Ala-NH₂ | 67 | 99.5 ± 4.5 | |
| 26326 | N-Ac-D- | DpClPhe, | D-3- | Ser, | c-PzACAla, | c-D- | Leu | ILys, | Pro, | D-Ala-NH₂ | 57 | 115.5 ± 2.4 | |

TABLE XIV-continued

LHRH analogs with 50% or more AOA at 0.25 ug

| IBR # | Sequence | | | | | | | | | | AOA/ 0.25 | Wheal area | ED |
|---|---|---|---|---|---|---|---|---|---|---|---|---|---|
| 26181 | N-Ac-D-2-Nal, | 2-Nal, DpClPhe, | Pal, D-3-Pal, | Ser, | PicLys | PzACAla c-D-PzACAla | Leu | IOrn | Pro, | D-Ala-NH$_2$ | 50 | 101.6 ± 2.2 | |
| *25933 | N-Ac-D-2-Nal, | 2-Nal, DpClPhe, | Pal, D-3-Pal, | Ser, | PicLys | D-PicLys | Leu | IOrn | Pro, | D-Ala-NH$_2$ | 50 | 113.0 ± 0 | |
| 26346 | N-Ac-D-2-Nal, | 2-Nal, DpClPhe, | Pal, D-3-Pal, | Ser, | PicLys | D-PicLys | Abu | Arg | Pro, | D-Ala-NH$_2$ | 50 | 113.2 ± 5.4 | |

*Claimed in original

What is claimed:

1. A process for inhibiting ovulation in an animal comprising administering to said animal a decapeptide having the structure: N-Ac-D-2Nal$^1$, D-pClPhe$^2$, D-3Pal$^3$, Ser$^4$, NicLys$^5$, D-NicLys$^6$, Leu$^7$, ILys$^8$, Pro$^9$ and D-Ala$^{10}$NH$_2$.

2. A process for inhibiting ovulation in an animal comprising administering to said animal a decapeptide having the structure: N-Ac-D-2Nal$^1$, D-pClPhe$^2$, D-3Pal$^3$, Ser$^4$, PicLys$^5$, D-PzACAla$^6$, Leu$^7$, ILys$^8$, Pro$^9$ and D-Ala$^{10}$NH$_2$.

3. A process for inhibiting the onset of puberty in an animal comprising administering to said animal a decapeptide having the structure: N-Ac-D-2Nal$^1$, D-pClPhe$^2$, D-3Pal$^3$, Ser$^4$, NicLys$^5$, D-NicLys$^6$, Leu$^7$, ILys$^8$, Pro$^9$ and D-Ala$^{10}$NH$_2$.

4. A process for inhibiting the sexual impetus of an animal comprising administering to said animal a decapeptide having the structure: N-Ac-D-2Nal$^1$, D-pClPhe$^2$, D-3Pal$^3$, Ser$^4$, NicLys$^5$, D-NicLys$^6$, Leu$^7$, ILys$^8$, Pro$^9$ and D-Ala$^{10}$NH$_2$.

5. A process for suppressing LH and FSH levels of an animal comprising administering to said animal an LHRH antagonist having low histamine releasing activity comprising a decapeptide of the formula AA$^1$-D-pClPhe$^2$-D-3Pal$^3$-Ser$^4$-AA$^5$-AA$^6$-AA$^7$-AA$^8$-Pro$^9$-D-Ala$^{10}$-NH$_2$, wherein AA$^1$ is N-Ac-D-2Nal, N-Ac-D-pClPhe or N-Ac-D-Cl$_2$Phe;

AA$^5$ is Tyr, NicLys, PicLys, MNicLys, MPicLys, INicLys, DMGLys, PzcLys, or c-PzACAla;

AA$^6$ is D-NicLys, D-PicLys, D-MNicLys, D-MPicLys, D-INicLys, D-BzLys, D-PzcLys, D-PzACAla, D-NACAla, or D-PACAla;

AA$^7$ is Leu, Aile, Nle, Val, NVal, Abu, or Ala; and

AA$^8$ is ILys or IOrn.

6. A process according to claim 5 wherein the decapeptide has the structure: N-Ac-D-2Nal$^1$, D-pClPhe$^2$, D-3Pal$^3$, Ser$^4$, NicLys$^5$, D-NicLys$^6$, Leu$^7$, ILys$^8$, Pro$^9$ and D-Ala$^{10}$NH$_2$.

7. A process for lowering LH and FSH levels in serum of post-menopausal woman comprising administering to said woman a decapeptide having the structure: N-Ac-D-2Nal$^1$, D-PclPal$^2$, D-3Pal$^3$, Ser$^4$, NicLys$^5$, NicLys$^6$, Leu$^7$, ILys$^8$, Pro$^9$ and D-Ala$^{10}$NH$_2$.

8. A process for inhibiting the growth of hormone-dependent tumors in an animal comprising administering to said animal a decapeptide having the structure: N-Ac-D-2-Nal$^1$, D-pClPhe$^2$, D-3Pal$^3$, Ser$^4$, NicLys$^5$, D-NicLys$^6$, Leu$^7$, ILys$^8$, Pro$^9$ and D-Ala$^{10}$NH$_2$.

9. A process according to claim 5, wherein said antagonist at a dosage of 1 µg has an antiovulatory activity of about 90% or higher.

10. A process according to claim 5 wherein said decapeptide has a histamine release corresponding to an ED$_{50}$ value of about 86 µg/mL or higher.

11. A process according to claim 5 wherein AA$^1$ is N-Ac-D-2Nal, AA$^5$ is DMGLys, AA$^6$ is D-NicLys, AA$^7$ is Leu, and AA$^8$ is ILys.

12. A process according to claim 5 wherein AA$^1$ is N-Ac-D-2Nal, AA$^5$ is PicLys, AA$^6$ is D-NicLys, AA$^7$ is Leu, and AA$^8$ is ILys.

13. A process according to claim 5 wherein AA$^1$ is N-Ac-D-2Nal, AA$^5$ is INicLys, AA$^6$ is D-INicLys, AA$^7$ is Leu, and AA$^8$ is ILys.

14. A process according to claim 5 wherein AA$^1$ is N-Ac-D-2Nal, AA$^5$ is NicLys, AA$^6$ is D-BzLys, AA$^7$ is Leu, and AA$^8$ is ILys.

15. A process according to claim 5 wherein AA$^1$ is N-Ac-D-2Nal, AA$^5$ is NicLys, AA$^6$ is D-PicLys, AA$^7$ is Leu, and AA$^8$ is ILys.

16. A process according to claim 5 wherein AA$^1$ is N-Ac-D-2Nal, AA$^5$ is NicLys, AA$^6$ is D-PzcLys, AA$^7$ is Leu, and AA$^8$ is ILys.

17. A process according to claim 5 wherein AA$^1$ is N-Ac-D-2Nal, AA$^5$ is NicLys, AA$^6$ is D-PzcLys, AA$^7$ is Leu, and AA$^8$ is IOrn.

18. A process according to claim 5 wherein AA$^1$ is N-Ac-D-2Nal, AA$^5$ is NicLys, AA$^6$ is D-PzACAla, AA$^7$ is Leu, and AA$^8$ is ILys.

19. A process according to claim 5 wherein AA$^1$ is N-Ac-D-2Nal, AA$^5$ is NicLys, AA$^6$ is D-NACAla, AA$^7$ is Leu, and AA$^8$ is ILys.

20. A process according to claim 5 wherein AA$^1$ is N-Ac-D-2Nal, AA$^5$ is PicLys, AA$^6$ is D-PicLys, AA$^7$ is Val, and AA$^8$ is ILys.

21. A process according to claim 5 wherein AA$^1$ is N-Ac-D-2Nal, AA$^5$ is PicLys, AA$^6$ is D-PicLys, AA$^7$ is Val, and AA$^8$ is IOrn.

22. A process according to claim 5 wherein AA$^1$ is N-Ac-D-2Nal, AA$^5$ is PicLys, AA$^6$ is D-PicLys, AA$^7$ is Aile, and AA$^8$ is ILys.

23. A process according to claim 5 wherein AA$^1$ is N-Ac-D-2Nal, AA$^5$ is PicLys, AA$^6$ is D-PicLys, AA$^7$ is Aile, and AA$^8$ is IOrn.

24. A process according to claim 5 wherein AA$^1$ is N-Ac-D-2Nal, AA$^5$ is PicLys, AA$^6$ is D-PicLys, AA$^7$ is Abu, and AA$^8$ is ILys.

25. A process according to claim 5 wherein AA$^1$ is N-Ac-D-2Nal, AA$^5$ is PicLys, AA$^6$ is D-PicLys, AA$^7$ is Abu, and AA$^8$ is IOrn.

26. A process according to claim 5 wherein AA$^1$ is N-Ac-D-2Nal, AA$^5$ is PicLys, AA$^6$ is D-PicLys, AA$^7$ is Nle, and AA$^8$ is ILys.

27. A process according to claim 5 wherein AA$^1$ is N-Ac-D-2Nal, AA$^5$ is PicLys, AA$^6$ is D-PicLys, AA$^7$ is NVal, and AA$^8$ is ILys.

28. A process according to claim 5 wherein AA$^1$ is N-Ac-D-2Nal, AA$^5$ is PicLys, AA$^6$ is D-PicLys, AA$^7$ is Ala, and AA$^8$ is ILys.

29. A process according to claim 5 wherein AA$^1$ is N-Ac-D-2Nal, AA$^5$ is PicLys, AA$^6$ is c-D-PzACAla, AA$^7$ is Leu, and AA$^8$ is ILys.

30. A process according to claim 5 wherein AA$^1$ is N-Ac-D-2Nal, AA$^5$ is PicLys, AA$^6$ is c-D-PzACAla, AA$^7$ is Leu, and AA$^8$ is IOrn.

31. A process according to claim 5 wherein AA$^1$ is N-Ac-D-2Nal, AA$^5$ is PicLys, AA$^6$ is c-D-PzACAla, AA$^7$ is Val, and AA$^8$ is ILys.

32. A process according to claim 5 wherein AA$^1$ is N-Ac-D-2Nal, AA$^5$ is PicLys, AA$^6$ is D-PACAla, AA$^7$ is Leu, and AA$^8$ is ILys.

33. A process according to claim 6 wherein AA$^1$ is N-Ac-D-2Nal, AA$^5$ is PicLys, AA$^6$ is t-D-PzACAla, AA$^7$ is Leu, and AA$^8$ is ILys.

34. A process according to claim 5 wherein AA$^1$ is N-Ac-D-2Nal, AA$^5$ is c-PzACAla, AA$^6$ is D-PicLys, AA$^7$ is Leu, and AA$^8$ is ILys.

35. A process according to claim 5 wherein AA$^1$ is N-Ac-D-2Nal, AA$^5$ is c-PzACAla, AA$^6$ is c-D-PzACAla, AA$^7$ is Leu, and AA$^8$ is ILys.

36. A process according to claim 5 wherein AA$^1$ is N-Ac-D-2Nal, AA$^5$ is c-PzACAla, AA$^6$ is D-PicLys, AA$^7$ is Val, and AA$^8$ is ILys.

37. A process according to claim 5 wherein AA$^1$ is N-Ac-D-2Nal, AA$^5$ is MPicLys, AA$^6$ is D-MPicLys, AA$^7$ is Leu, and AA$^8$ is ILys.

38. A process according to claim 5 wherein AA$^1$ is N-Ac-D-2Nal, AA$^5$ is DMGLys, AA$^6$ is D-BzLys, AA$^7$ is Leu, and AA$^8$ is ILys.

39. A process according to claim 5 wherein AA$^1$ is N-Ac-D-2Nal, AA$^5$ is Tyr, AA$^6$ is D-NicLys, AA$^7$ is Leu, and AA$^8$ is ILys.

40. A process according to claim 5 wherein AA$^1$ is N-Ac-D-2Nal, AA$^5$ is Tyr, AA$^6$ is D-NicLys, AA$^7$ is Leu, and AA$^8$ is IOrn.

41. A process according to claim 5 wherein AA$^1$ is N-Ac-D-2Nal, AA$^5$ is Tyr, AA$^6$ is c-D-PzACAla, AA$^7$ is Leu, and AA$^8$ is ILys.

42. A process according to claim 5 wherein the suppressed LH and FSH levels of an animal results in inhibiting ovulation, inhibiting the onset of puberty, inhibiting sexual impetus, or inhibiting the growth of hormone dependent tumors.

43. A process for inhibiting ovulation in an animal comprising administering to said animal an LHRH antagonist having low histamine releasing activity comprising a decapeptide of the formula AA$^1$-D-pClPhe$^2$-D-3Pal$^3$-Ser$^4$-AA$^5$-AA$^6$-AA$^7$-AA$^8$-Pro$^9$-D-Ala$^{10}$-NH$_2$, wherein AA$^1$ is N-Ac-D-2Nal, N-Ac-D-pClPhe or N-Ac-D-Cl$_2$Phe;

AA$^5$ is Tyr, NicLys, PicLys, MNicLys, MPicLys, INicLys, DMGLys, PzcLys, or c-PzACAla;

AA$^6$ is D-NicLys, D-PicLys, D-MNicLys, D-MPicLys, D-INicLys, D-BzLys, D-PzcLys, D-PzACAla, D-NACAla, or D-PACAla;

AA$^7$ is Leu, Aile, Nle, Val, NVal, Abu, or Ala; and

AA$^8$ is ILs or IOrn.

* * * * *

UNITED STATES PATENT AND TRADEMARK OFFICE
CERTIFICATE OF CORRECTION

PATENT NO.   :   5,763,404
DATED        :   JUNE 9, 1998
INVENTORS    :   Karl A. Folkers/Cyril Y. Bowers/Anders Ljungqvist/Pui-Fun Louisa Tang/
                 Minoru Kubota/Dong-Mei Feng It is certified that error appears in the above-identified patent and that said Letters Patent is hereby corrected as shown below:

On the face of the patent, the Assignees should be listed as follows:

Board of Regents, The University of Texas System
    Austin, Texas

The Administrators of the Tulane Educational Fund
    New Orleans, Louisiana --; and before the abstract, insert -- Attorney, Agent, or Firm -- Arnold, White & Durkee --
In claim 33, line 1, "claim 6" should read --claim 5--.

In claim 43, line 14, "ILs" should read --ILys--.

Signed and Sealed this

Twenty-fifth Day of August, 1998

*Attest:*

BRUCE LEHMAN

*Attesting Officer*      *Commissioner of Patents and Trademarks*